(12) United States Patent
Bernard et al.

(10) Patent No.: US 7,919,292 B2
(45) Date of Patent: Apr. 5, 2011

(54) **PRODUCING HYDROGEN BY HETEROLOGOUS EXPRESSION OF A TYPE II NAD (P)H DEHYDROGENASE IN *CHLAMYDOMONAS***

(75) Inventors: Laetitia Bernard, Manosque (FR); Florence Mus, Saint Paul lez Durance (FR); Carine Simon-Desplats, La Seyne-sur-Mer (FR); Stephan Cuine, Manosque (FR); Laurent Cournac, La Tour d'Aigues (FR); Gilles Peltier, Pierrevert (FR)

(73) Assignee: Commissariat a l'Energie Atomique, Paris (FR)

( * ) Notice: Subject to any disclaimer, the term of this patent is extended or adjusted under 35 U.S.C. 154(b) by 250 days.

(21) Appl. No.: 11/577,038

(22) PCT Filed: Oct. 11, 2005

(86) PCT No.: PCT/FR2005/002511
§ 371 (c)(1),
(2), (4) Date: Sep. 12, 2007

(87) PCT Pub. No.: WO2006/040471
PCT Pub. Date: Apr. 20, 2006

(65) Prior Publication Data
US 2008/0199928 A1 Aug. 21, 2008

(30) Foreign Application Priority Data
Oct. 11, 2004 (FR) .................................... 04 10715

(51) Int. Cl.
*C12P 3/00* (2006.01)
*C12N 15/74* (2006.01)
*C12N 1/13* (2006.01)
(52) U.S. Cl. ...................... 435/168; 435/471; 435/257.2
(58) Field of Classification Search ........................ None
See application file for complete search history.

(56) References Cited

U.S. PATENT DOCUMENTS
4,532,210 A 7/1985 Miura et al.
2001/0053543 A1 12/2001 Anastasios et al.

FOREIGN PATENT DOCUMENTS
WO  WO 03/067213  8/2003

OTHER PUBLICATIONS

International Search Report for PCT/FR2005/002511 filed Oct. 11, 2005.
L. Cournac et al., "Limiting Steps of Hydrogen Production in *Chlamydomonas reinhardtii* and Synechocystis PCC 6803 as Analysed by Light-Induced Gas Exchange Transients"; International Journal of Hydrogen Energy; vol. 27, 2002, pp. 1229-1237, XP002329973.
L. Cournac et al., "Interactions Between Chlororespiration, Photosynthesis, and Hydrogen Production in *Chlamydomonas reinhardtii*"; Photosynthesis Research; vol. 69, No. 1-3, 2001, p. 257, XP002329974.
Peltier Gilles et al.; "Chlororespiration"; Annual Review of Plant Biology. vol. 53 Annual Reviews, 4139 El Camino Way, P.O. Box 10139, Palo Alto, CA, 94303-0139, USA Series, Annual Review of Plant Biology; 2002, pp. 523-550, XP002329975.
Database EMBL; Jul. 5, 2004; B. Goodner, et al.; "AGR_C_3667p", XP002329976.
B. Goodner et al.; "Genome Sequence of the Plant Pathogen and Biotechnology Agent Agrobacterium Tumefaciens C58"; Science; vol. 294, 2001, pp. 2323-2328.
Mus F et al.; "Inhibitor Studies on Non-Photochemical Plastoquinone Reduction and H2 Photoproduction in *Chlamydomonas reinhardtii*"; Biochimica et al Biophysica Acta. Bioenergetics, Amsterdam, NL; vol. 1708, No. 3, May 26, 2005, pp. 322-332, XP004971733.

*Primary Examiner* — Nancy Vogel
(74) *Attorney, Agent, or Firm* — Alston & Bird LLP

(57) ABSTRACT

The invention concerns the use of a type II NAD(P)H dehydrogenase (NDH-II), or of a polynucleotide encoding said NDH-II, to increase the capacity of a green algae to produce hydrogen. Said polynucleotide is in particular useful for transforming said green algae, so as to improve its hydrogen production.

7 Claims, 10 Drawing Sheets

```
NC-NDI1  (EAA27430)   ANLLHFAIVGGGPTGIEYASELHDLIHDDLSKMYP-DLLKFVRITVYQVSPKVLP
N2Cr2                 KKLLTFVVGGGPTGVEVAAELYDMIEEDLSKLYP-NLVKDVSIQVELMDHVLS
ST-NDB1  (CAB52797)   RTNLHFVIVGGGPTGVEFAAELHDYVYEDLVKIYP-SVKDFVKITVIQSGDHILN
SC-NDE1  (NP_013865)  ARLLSFVVVGGGPTGVEFAAELRDYVDQDLRKWMP-ELSKEIKVTLVEALPNILN
SC-NDE2  (NP_010198)  KRLLTFVVVGGGPTGVEFAAELQDYINQDLRKWMP-DLSKEMKVILIGALPNILN
YL-NDH2  (XP_505856)  KRLLHTVVVGGGPTGVEFAAELQDFEEDDLRKWIP-DIRDDFKVTLVEALPNVLP
SC-NDI1  (NP_013586)  RRLLSIVVVGGGPTGVEAAGELQDYVHQDLRKFLP-ALAEEVQIHLVEALPIVLN
NC-NDE1  (CAB41986)   KRLLSFVVCGGGPTGVEFAAELEDLLNEDLTLHFPRLLRNEISVHLIQSRDHILN
ATUNDH2  (AI2824)     QALTFVIIGAGPTGVEMAGMIAELAHRALPAEFRNVDTRKTRVLLVEAGPRVLP
EC-NDH   (NP_415627)  NGKVNIAIVGGGATGVELSAELHNAVKQLHSYGYKGLTNEALNVTLVHAGERILP
Slr1743  (BAA17783)   AEKIRIAIVGGGYSGVELAAKLGDRL--------GERG------RIRIIEGKEILAM

Consensus             -----ΦΔ-Δ-G--G---G---Δ---Δ---------------------Δ-Δ-----⊠
                           beta              alpha                beta
```

FIG. 2

A
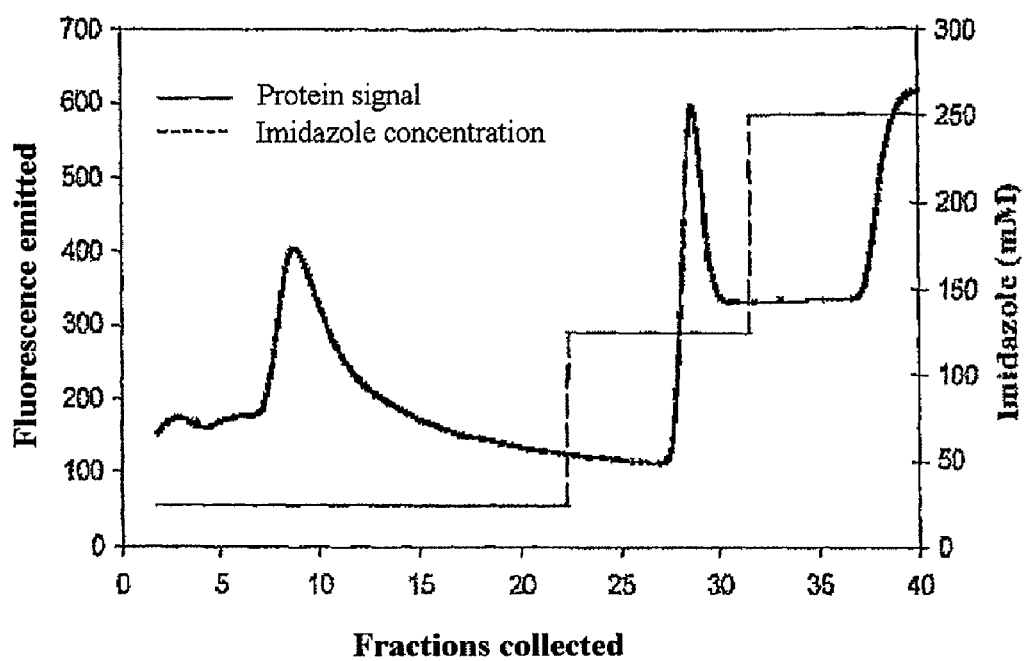
B
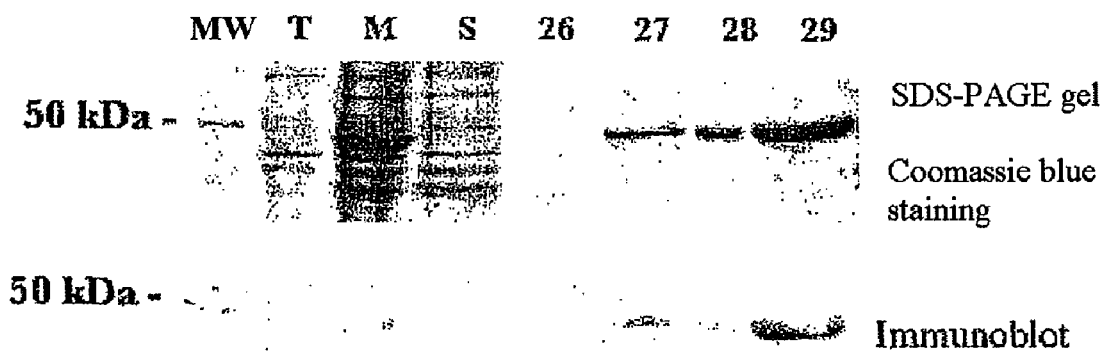
FIG. 3

FIG. 8
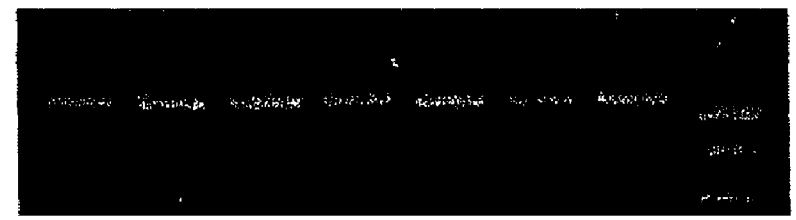
FIG. 9

A
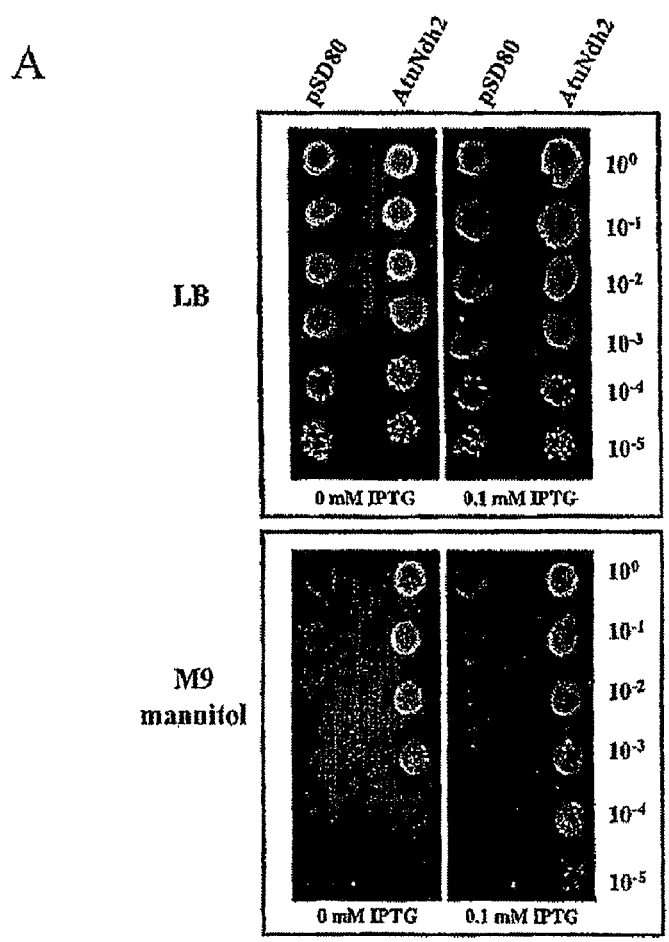
B
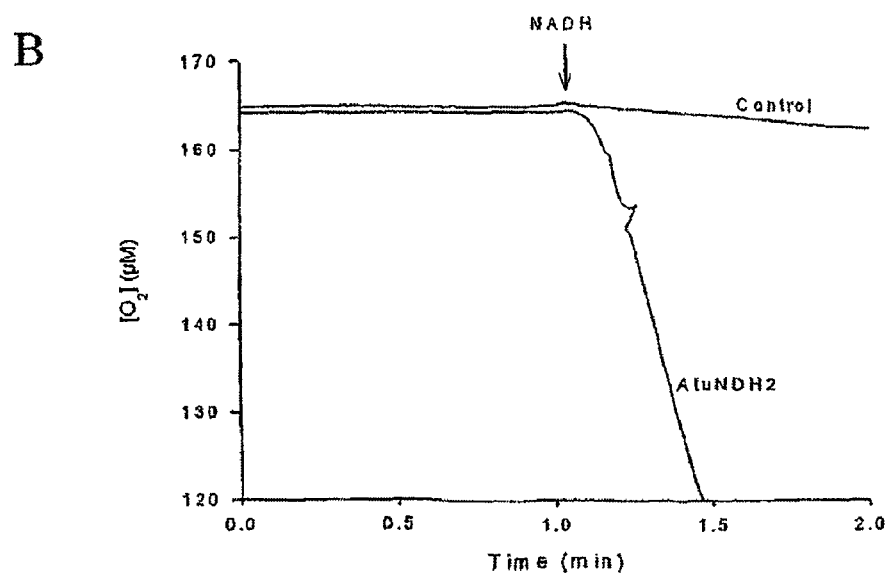
FIG 10

PRODUCING HYDROGEN BY HETEROLOGOUS EXPRESSION OF A TYPE II NAD (P)H DEHYDROGENASE IN *CHLAMYDOMONAS*

REFERENCE TO SEQUENCE LISTING SUBMITTED ELECTRONICALLY

The official copy of the sequence listing is submitted electronically via EFS-Web as an ASCII formatted sequence listing with a file named "326635-SEQLIST.txt", created on Apr. 10, 2007, and having a size of 28 kilobytes and is filed concurrently with the specification. The sequence listing contained in this ASCII formatted document is part of the specification and is herein incorporated by reference in its entirety.

FIELD AND BACKGROUND OF THE INVENTION

The present invention relates to the improvement of hydrogen production by *Chlamydomonas reinhardtii*.

Hydrogen is an essential starting material for the chemical industry, and also constitutes a fuel called upon to play a major role in the coming decades. Hydrogen-fed fuel cells make it possible, through the reaction of hydrogen with oxygen from the air, to produce electricity in a nonpolluting manner, while producing only steam as waste. The technological advances in the field of fuel cells make their use on a large scale increasingly foreseeable.

However, the majority of the hydrogen currently used is produced from fossil energy sources, such as petroleum or carbon, by techniques that themselves generate pollution, such as catalytic conversion of hydrocarbons from natural gas or cracking petroleum or carbon.

It therefore appears desirable to provide cost-effective processes for producing hydrogen from a renewable and clean primary energy source (that does not release greenhouse gases).

Certain unicellular green algae belonging to the genera *Scenedesmus, Chlorococcum, Chlorella* (order Chlorococcales), *Lobochlamys* and *Chlamydomonas* (order Volvocales), such as the species *Chlamydomonas reinhardtii*, are capable of producing hydrogen from solar energy, using water as electron and proton donor.

In these algae, the hydrogen is produced by an iron hydrogenase with a strong specific activity. This enzyme is connected to the PSI photosynthetic electron transfer chain via a common electron transporter, ferredoxin. The electrons required for the production of hydrogen can be supplied to PSI either through the activity of PSII (pathway A), or through the use of carbon stores via the nonphotochemical reduction of plastoquinones (pathway B). These two pathways are shown schematically in FIG. 1.

Legend of FIG. 1: In solid lines, pathway A, PSII-dependent; in dashed lines, pathway B, based on plastoquinone reduction, PSII-independent.

PSI: photosystem I; PSII: photosystem II; RuBP: ribulose 1,5-bisphosphate; LHC: light harvesting complex; FNR: ferredoxin NADP reductase; Fd: ferredoxin; Pc: plastocyanin; cytb6: cytochrome b6; cytf: cytochrome f; NDH: NADH-dehydrogenase; $PQ(H)_2$: plastoquinol; Qa: quinone a; P680 and P700: reaction centers for PSI and PSII, respectively.

Under natural conditions, $H_2$ production is only a transient phenomenon. In fact, the hydrogenase is very sensitive to $O_2$. Now, the photolysis of water occurring within photosystem II, which supplies electrons for the production of $H_2$ via pathway A, also produces $O_2$, which induces a rapid inhibition of the hydrogenase.

Various solutions have been proposed in order to remedy this problem. The first solution is based on production in the dark, the others on production under light using in part pathway B, which, unlike pathway A, does not lead to oxygen production.

For example, U.S. Pat. No. 4,532,210 describes a process alternating light and dark phases. During the light periods, the algae produce $O_2$ and accumulate hydrocarbon-based stores produced by photosynthesis. These stores are then used under anaerobic conditions during the dark phases in order to produce hydrogen. This method requires a nitrogen purge in order to achieve the anaerobiosis. It is also limited by the efficiency of $H_2$ production in the dark, which is an order of magnitude lower than production under light.

U.S. application 2001/0053543 describes a process based on the reversible inhibition of photosystem II by means of a sulfur deficiency. This process comprises a step consisting in culturing green algae, under light, and in a medium with a normal sulfur content, so as to allow the accumulation of hydrocarbon-based stores, and a step consisting in culturing in sealed containers, and under light, in a medium lacking sulfur. The inhibition of photosystem II leads to an arrest of oxygen production by photosynthesis. When the algae (in which respiration is not inhibited by the sulfur deficiency) have used all the oxygen present in the medium, they become anaerobic and use the hydrocarbon-based stores produced due to photosynthesis, to produce $H_2$. Alternation of phases of culturing in the presence and absence of sulfur makes it possible to temporally separate the light phases of $O_2$ production and $H_2$ production.

U.S. application 2003/0162273 proposes an alternative method for inducing a sulfur deficiency that inhibits photosystem II; it involves the use of a genetically modified alga underexpressing a chloroplast sulfate permease.

The methods described above make it possible to prevent inhibition of the iron hydrogenase by separating the production of $O_2$ and that of $H_2$. However, the production of hydrogen by the three methods described above has limitations. The first method is based on the fermentative activity of the alga in the dark, a relatively ineffective phenomenon that results in only marginal production of hydrogen. The second and third methods are based on the parallel functioning of pathways A and B. Pathway A, which is accompanied by oxygen release, must be maintained at a level below respiratory $O_2$ consumption in order to maintain anoxia. Pathway A is therefore limited by the respiratory capacity of the algae. The contribution of pathway B is significant but limited.

The aim of the present invention is to improve the yield of this second pathway (B). With this aim, the inventors had the idea of using, in the chloroplast, a type II NADH-dehydrogenase for stimulating the plastoquinone reduction reaction.

Type I and II NADH dehydrogenases are enzymes capable of reducing the quinones of electron transport chains. They are associated with mitochondrial and bacterial respiratory chains (KERSCHER, Biochim. Biophys. Acta 1459: 274-283, 2000).

Type I NADH dehydrogenases (NDH-I) are multimeric transmembrane complexes comprising from 14 to approximately 50 subunits. This type of complex oxidizes only NADH and has an associated proton pumping activity.

Type II NAD(P)H dehydrogenases (NDH-II) are monomeric enzymes of oxidoreductase type, which have a molecular weight of between 30 and 60 kDa and are capable of reducing the quinones of bacterial respiratory chains or mitochondrial chains of plants and yeasts, by oxidizing NADH or NADPH. Their association with the photosynthetic chains of plants and algae has also been proposed, but has not been demonstrated to date. This type of enzyme has not been demonstrated in the animal kingdom.

In the chloroplasts of higher plants, the existence of a functional NDH-I complex has been demonstrated (BURROWS et al., EMBO J. 17: 868-876, 1998; SAZANOV et al., Proc. Natl. Acad. Sci. USA 95: 1319-1324, 1998; HORVATH et al., Plant Physiol. 123: 1337-1349, 2000) and the existence of an NDH-II-type activity has also been proposed (CORNEILLE et al., Biochim. Biophys. Acta 1363: 59-69, 1998). In *Chlamydomonas reinhardtii*, the genes encoding the chloroplast NDH-I complex are absent. However, existence of an NDH-II-type activity has been suggested (COURNAC et al., Int. J. Hydrog. Energy 27: 1229-1237, 2002; PELTIER and COURNAC, Annu. Rev. Plant Biol. 53: 523-550, 2002).

SUMMARY OF THE INVENTION

A subject of the present invention is thus the use of a type II NAD(P)H dehydrogenase (NDH-II), or of a polynucleotide encoding said protein, for increasing the capacity of a green alga to produce hydrogen.

According to a preferred embodiment of the present invention, said green alga is a unicellular green alga, preferably chosen from the Chlorococcales, in particular the genera *Scenedesmus, Chlorococcum* and *Chlorella*, and the Volvocales, in particular the genera *Lobochlamys* and *Chlamydomonas*.

According to a preferred arrangement of this embodiment, said alga belongs to the genus *Chlamydomonas*. Advantageously, said alga belongs to the species *Chlamydomonas reinhardtii*.

The definition "NDH-II" is given to any flavoenzyme having:
a) characteristics common to all the NAD(P)H dehydrogenases, i.e. i) the ability to catalyze the reduction of quinones of electron transport chains through the oxidation of NADH or of NAD(P)H, using FAD or FMN as flavin cofactor, and ii) the presence, in its sequence, of at least one copy of the consensus motif GxGxxG where "G" represents a glycine and "x" represents any amino acid, which corresponds to the binding site for the flavin cofactor and for NAD(P)H;
b) characteristics specific to type II NAD(P)H dehydrogenases, i.e. the activity in the form of a monomer of 30 to 60 kDa or of a homodimer, the fact of not carrying out any transmembrane proton transport, and the fact of having a rotenone-insensitive activity.

For a detailed review concerning NDH-IIs, reference may in particular be made to the reviews by YAGI (J. Bioenergetics Biomembranes 23: 211-224, 1991), by KERSCHER (Biochim. Biophys. Acta 1459: 274-283, 2000), and by MELO et al. (Microbiol Mol Biol Rev. 68: 603-616, 2004).

The inventors have thus used the NDH-II from *Agrobacterium tumefaciens* (NCBI accession No.: AI2824; SWISSPROT accession No.: Q8UDU6), also referred to hereinafter as Agtundh2. The nucleotide sequence encoding this enzyme is represented in the attached sequence listing under the number SEQ ID NO: 1, and the deduced polypeptide sequence under the number SEQ ID NO: 2.

Other NDH-IIs that can be used for implementing the present invention are, by way of nonlimiting examples, the NDH-IIs from *Acidianus ambivalens* (AJ489504), from *Corynebacterium glutamicum* (CAB41413.1), from *Escherichia coli* (NP_415627), from *Synechocystis* sp. (HOWITT et al., J. Bacteriol. 181(13): 3994-4003, 1999; ORF slr1743: BAA17783), from *Zymomonas mobilis* (AAD56918), from *Bacillus subtilis* (NP_389111), from *Azotobacter vinelandi* (AAK19737), from *Trypanosoma brucei* (AAM95239.1), from *Solanum tuberosum* (CAB52796.1, CAB52797.1), from *Saccharomyces cerevisiae* (YML120C (NP_013586), YMR145c (NP_013865.1), YDL085w (NP_010198.1)), from *Neurospora crassa* (CAB41986, EAA27430), and from *Yarrowia lipolytica* (XP_505856).

Advantageously, an endogenous *Chlamydomonas reinhardtii* NDH-II can also be used. Sequences encoding putative NDH-IIs have been identified in the complete sequence of the *Chlamydomonas reinhardtii* genome (version 2) on the site "http://genome.jgi-psf.org/chlre2/chlre2.home.html", under the identifiers C_310108, C_1170009, C_5950001, C_1890016, C_1450028, C_1450029 and C_270109. Based on these sequences, the inventors have identified a sequence effectively encoding an NDH-II. This sequence, hereinafter referred to as N2Cr2, is represented in the attached sequence listing under the number SEQ ID NO: 3, and the deduced polypeptide sequence, referred to as N2Cr2, is represented under the number SEQ ID NO: 4.

The inventors have cloned and expressed a fragment of N2Cr2 corresponding to nucleotides 199-1857 of the sequence SEQ ID NO: 3 (and therefore encoding a polypeptide corresponding to amino acids 67-619 of the sequence SEQ ID NO: 4) and have shown that the polypeptide encoded by this fragment corresponds to a chloroplast-located NDH-II.

The NDH-II N2Cr2, and any fragment of this protein exhibiting NAD(P)H dehydrogenase activity, and the polynucleotides encoding said NDH-II or said fragment, are also part of the subject of the present invention.

A certain number of the NDH-IIs mentioned above have a preferential affinity for NADH. Now, although NADH and NADPH are both present in the chloroplast, it is NADPH which represents the predominant form. For the purpose of increasing the efficiency, in a chloroplast context, of NDH-IIs that preferentially use NADH, the inventors had the idea of modifying these enzymes, in order to increase their efficiency for NADPH.

They have carried out a site-directed mutagenesis of Agtundh2, and have shown that substitution of the acid residue (glutamate in the case of Agtundh2) located, in enzymes that preferentially use NADH, at the end of the second beta-sheet of the pyridine-nucleotide-binding beta-alpha-beta motif (also called "Rossman motif"), with a neutral polar residue such as those encountered at the same position in enzymes that preferentially use NADPH, makes it possible to increase its affinity for NADPH.

A subject of the present invention is therefore also a mutant NDH-II, obtained from an NDH-II that preferentially uses NADH, by substitution of the glutamate or aspartate residue located at the end of the second beta-sheet of the pyridine-nucleotide-binding beta-alpha-beta motif, with a neutral polar residue, preferentially a glutamine or asparagine residue.

This residue corresponds, for example, to position 201 of the sequence of Agtundh2 (SEQ ID NO: 2), and to position 285 of the sequence of N2Cr2 (SEQ ID NO: 4).

FIG. 2 represents an alignment of the sequences of various NDH-IIs, at the level of the pyridine-nucleotide-binding site. The consensus sequence of the beta-alpha-beta motif is represented below the sequence alignment; Φ represents a hydrophilic residue; A represents a hydrophobic residue and # represents the residue located at the end of the second beta-sheet; it is an acidic residue in NDH-IIs that preferentially use NADH, and a neutral polar residue in NDH-IIs that preferentially use NADPH (for example, as shown by the alignment in FIG. 2, the NDH-IIs ST-NDB1 and NC-NDE1 have a glutamine residue at this position).

A subject of the present invention is a method for increasing the capacity of a green alga to produce hydrogen, characterized in that it comprises the genetic transformation of said alga with a polynucleotide encoding an NDH-II as defined above, and the expression of said NDH-II in said alga.

In order to implement the present invention, the usual genetic engineering techniques will be used. Conventionally, an expression cassette is constructed by placing a polynucleotide encoding the NDH-II that it is desired to express, under the control of suitable expression regulatory sequences (in particular, transcription promoter and terminator). Advantageously, said polynucleotide encoding the NDH-II is fused to a chloroplast-targeting sequence.

The expression cassette may also comprise, in addition, transcription and/or translation regulatory elements, among which mention will in particular be made of transcription enhancers or silencers, leader sequences, polyadenylation sequences, etc.

The expression cassette thus obtained is then inserted into a suitable vector, which is used to transform the chosen host organism or cell.

Various tools and methods that can be used for transforming green algae are known in themselves, and can be used for the implementation of the present invention (for review, ROCHAIX et al., *The Molecular Biology of Chloroplasts and Mitochondria in Chlamydomonas*, Kluwer Academic Publishers, The Netherlands, 1998).

By way of nonlimiting examples of expression-regulating sequences (promoters, terminators, etc.) and chloroplast-targeting sequences that can be used in the context of the present invention, mention will be made of:

for nuclear expression, the promoters, terminators and targeting peptides of the RbcS2 gene encoding the RUBISCO (ribulose bisphosphate carboxylase/oxygenase) small subunit (GOLDSCHMIDT-CLERMONT and RAHIRE, J. Mol. Biol. 191: 421-432, 1986), the AtpC gene encoding the gamma subunit of chloroplast ATP synthetase (QUINN and MERCHANT, Plant Cell 7: 623-638, 1995; KINDLE and LAWRENCE. Plant Physiol. 116: 1779-1791, 1998), and the PetE gene encoding plastocyanin (QUINN and MERCHANT, 1995, mentioned above; KINDLE, Plant Mol. Biol. 38: 365-377, 1998), which can be combined differently; and for expression in chloroplasts, the promoters, terminators and targeting peptides of the RbcL gene encoding the RUBISCO large subunit, the AtpB gene encoding the beta subunit of ATP synthetase, and the PsbA gene encoding the D1 subunit of photosystem II (BATEMAN and PURTON, Mol. Gen. Genet. 263: 404-410, 2000).

By way of nonlimiting examples of selectable markers that can be used in the context of the present invention, mention will be made of:

for nuclear expression, the Arg7 gene encoding *Chlamydomonas* arginosuccinate lyase which complements a mutant that is deficient in and therefore auxotrophic for arginine (DEBUCHY et al., EMBO J. 8: 2803-2809, 1989), the Nit 1 gene encoding *Chlamydomonas* nitrate reductase which complements a mutant that is deficient and therefore incapable of growing with nitrates as the sole source of nitrogen (KINDLE et al., J. Cell Biol. 109: 2589-2601, 1989), the Nic7 gene encoding an enzyme involved in nicotinamide biosynthesis from *Chlamydomonas* which complements a mutant that is deficient and therefore auxotrophic for nicotinamide (FERRIS, Genetics 141: 543-549, 1995), the Oee1 gene encoding a subunit of *Chlamydomonas* photosystem II which complements a strictly heterotrophic mutant (MAYFIELD and KINDLE, Proc. Natl. Acad. Sci. USA. 87: 2087-2091, 1990), the aadA gene encoding aminoglycoside adenine transferase from *E. coli* which confers spectinomycin and streptomycin resistance on any strain of *Chlamydomonas* (CERUTTI et al., Genetics. 145: 97-110, 1997), the ble gene encoding a bleomycin-binding protein from *Streptoalloteichus hindustanus* which confers phleomycin resistance on any strain of *Chlamydomonas* (STEVENS et al., Mol. Gen. Genet. 251: 23-30, 1996); genes encoding resistances to antibiotics must be expressed under the control of regulatory sequences from *Chlamydomonas*, such as those of RbcS2; and for expression in chloroplasts, complementation of a mutant obtained by deletion or insertion in a gene encoding a protein of the photosynthetic chain, by the natural gene carried by the inserted DNA fragment, for example the psbH gene encoding a subunit of PSII (BATEMAN and PURTON, Mol. Gen. Genet. 263: 404-410, 2000), the aadA gene encoding aminoglycoside adenine transferase from *E. coli*, which confers streptomycin and spectinomycin resistance, and the aphA-6 gene encoding aminoglycoside phosphotransferase from *Acinetobacter baumanii*, which confers kanamycin and amikacin resistance.

The transformation of the green algae can be carried out by various methods, such as, for example, the insertion of a DNA into the nuclear genome by transformation of glass beads (KINDLE, Proc. Natl. Acad. Sci. USA. 87: 1228-1232, 1990), by biolistics (DEBUCHY et al., EMBO J. 8: 2803-2809, 1989), and by electroporation (SHIMOGAWARA et al., Genetics. 148: 1821-1828, 1998).

For the transformation of the chloroplast DNA, and expression in chloroplasts, use can advantageously be made of the insertion, by homologous recombination, of a DNA ordered by sequences homologous to the sequence of the chloroplast genome and corresponding to neutral zones of the genome (noncoding and nonregulatory), and also the transformation techniques mentioned above for insertion into the nuclear genome, in particular biolistics, which gives the best yields.

The invention also relates to the green algae transformed with a polynucleotide encoding an NDH-II as defined above.

The green algae in accordance with the invention can be used for the production of hydrogen, under the same conditions as the nontransformed green algae. They can, for example, be used in the context of processes such as those described in U.S. Pat. No. 4,532,210 or application US 2001/0053543 mentioned above.

BRIEF DESCRIPTION OF THE DRAWINGS

The present invention will be understood more fully from the additional description and examples which follow, and from the accompanying drawings, in which:

FIG. 2 represents an alignment of the sequences of various NDH-IIs at the level of the pyridine-nucleotide-binding site. The sequences labeled as Nc-NDI1, N2Cr2, ST-NDB1, SC-NDE1, SC-NDE2, YL-NDH2, SC-NDI1, NC-NDE1, ATUNDH2, EC-NDH, and Sir1743 in FIG. 2 correspond to SEQ ID NOS: 28-38, respectively, in the Sequence Listing.

FIG. 3A is a chromatogram trace for a purified enzyme of Example 1 (II).

FIG. 3B is a gel electrophoresis of the protein content.

FIG. 8 is a gel electrophoresis of amplification products of Example 3.

FIG. 9 is a gel electrophoresis of amplification products of Example 3.

FIG. 10A illustrates cultures used in Example 4.

FIG. 10B is a graph illustrating the oxygen uptake activity in Example 4.

Figure 1:
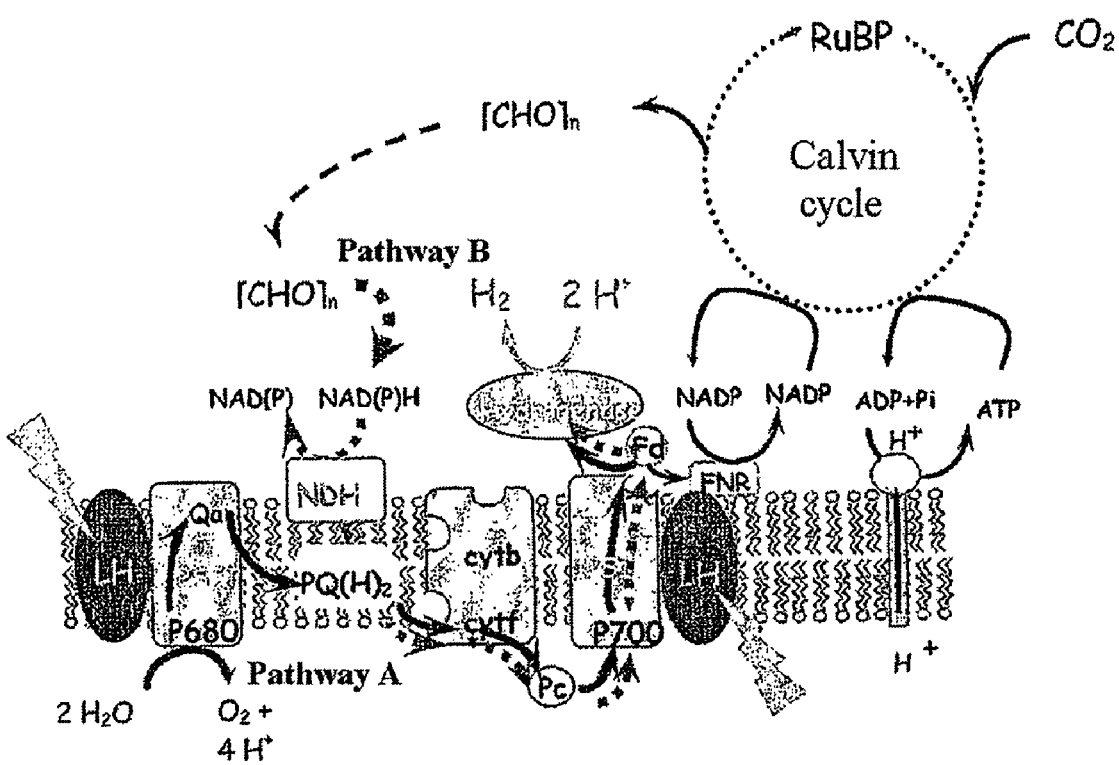
FIG. 1 schematically illustrates two pathways for electron transfer required for the production of hydrogen.

The present invention will be understood more thoroughly from the additional description which follows, which refers to nonlimiting examples showing the capacity of an *Agrobacterium* NDH-II to interact with the photosynthetic electron transport chain of *Chlamydomonas reinhardtii* and to reduce plastoquinones, and illustrating the transformation of *Chlamydomonas reinhardtii* with a polynucleotide encoding said NDH-II.

EXAMPLE 1

Cloning and Expression in *E. coli* of the NDH-II of *Agrobacterium tumefaciens*

I—Isolation of the NDH-II Gene

The Agtundh2 gene encoding the NDH-II of *Agrobacterium tumefaciens* (NCBI accession No.: AI2824; SWIS-SPROT accession No.: Q8UDU6) was amplified from the genomic DNA of *Agrobacterium tumefaciens* (strain C58) using the following pair of primers:

```
Sense: N2Ag.mfe.F
                                         (SEQ ID NO: 5)
CGCCAATTGATGCAAGAACATCATGTT Antisense: N2Ag.6His.PstR
                                         (SEQ ID NO: 6)
AAAACTGCAGTCAATGATGATGATGATGATGGGCCTCGTCCTTCAGCG
```

The mfeI and PstI (in italics) restriction sites were inserted into the sense and antisense primers, respectively upstream and downstream of the start and stop codons (in bold). A tag composed of 6 histidine codons (underlined) was inserted upstream of the stop codon. The amplification was carried out under the following conditions:

Reaction Mix:
Specific reaction buffer containing 1.5 mM $MgCl_2$
Primers at 0.5 µM final concentration
dNTP mix at 200 µM final concentration
300 ng of DNA
1.5 units of Expand High Fidelity Taq polymerase (Roche)
Amplification Conditions:
3 min at 95° C.+1 min at 80° C.: 1 cycle
1 min at 95° C.+1 min at 70° C. (−0.5° C. at each cycle)+2 min at 72° C.: 20 cycles
1 min at 95° C.+1 min at 60° C.+2 min at 72° C.: 10 cycles
6 minutes at 72° C.: 1 cycle.

The amplification product comprises the sequence encoding the NDH-II, and, 3' of the latter, a sequence encoding a tag composed of 6 histidine codons.

II—Expression in *E. coli* and Purification

1—Cloning

The amplification product was digested with mfeI and PstI (New England Biolab, protocol recommended by the supplier) and introduced by ligation (ligase from New England Biolab, protocol recommended by the supplier) into an expression vector digested with EcoRI and PstI.

This vector, pSD80, carries an ampicillin-resistance cassette, a strong Taq promoter and the Laq iQ repressor gene (PATEL and DUNN, J. Bacteriol. 177: 3917-3922, 1995; SMITH et al., Biochem. 35: 8805-8814, 1996).

The ligation product was then introduced by electroporation into *E. coli* DH10β.

The ampicillin-resistant transformants were then screened by PCR using the same primers and the same conditions as indicated above, in order to verify the presence of the Agtundh2 gene.

The construct was then verified by sequencing using primers specific for the pSD80 vector and also primers internal to the Agtundh2 gene.

```
PSD80.F
5'-GAGCTGTTGACAATTAAT-3'       (SEQ ID NO: 7)

PSD80.R
5'-AGGACGGGTCACACGCGC-3'       (SEQ ID NO: 8)

N2Ag.307.F
5'-TGGCCACCGGCGCGCGT-3'        (SEQ ID NO: 9)

N2Ag.650.f
5'-TGCGAAGGAAGCGCTTGA-3'       (SEQ ID NO: 10)

N2Ag.901.R
5'-TTCCTGATTGACCGCGG-3'        (SEQ ID NO: 11)
```

After having verified that the sequence and the insertion were correct, this plasmid was named pSDN2Ag6H and was used to cotransform, by electroporation, the *E. coli* DH10β strain with a vector (pRare, Novagen) carrying the 6 most rare tRNAs of *E. coli*.

One of the cotransformants resistant to ampicillin and to chloramphenicol was chosen for the expression and purification of the NDH-II 6His protein.

2—Expression

A culture of LB (Luria Bertani) medium, in the presence of ampicillin and chloramphenicol, at a volume of 1 l in a 2.5 l Erlenmeyer flask, was inoculated at 1/50 from a 15 h preculture, and incubated at 37° C. with vigorous shaking, until an optical density of 0.5 was obtained.

The expression of NDH-II 6His was induced for 2 h with 0.5 mM of isopropylthio-β-D-galactoside (IPTG).

The cells were then collected by centrifugation and rinsed with new culture medium and stored at −80° C.

3—Purification

The purification protocol has been published by BJÖRK-LÖF et al. (FEBS Letts., 467: 105-110, 2000).

The cells were thawed and resuspended in 2.5 mM EDTA, 0.2 mM PMSF (phenylmethylsulfonyl fluoride), 200 mM Tris-Cl, pH 8, at the concentration of approximately 1 g per 10 ml. 300 µg/ml of lysozyme were added, and the mixture was incubated for 1 h in ice.

The suspension was then centrifuged for 60 min at 120 000×g. The pellet was subjected to an osmotic shock by resuspension in a 10 mM potassium phosphate buffer, pH 8, containing 2 mM EDTA and 0.2 mM PMSF, and homogenized with a Potter homogenizer, and then recentrifuged (60 min, 120 000×g).

The membrane fraction was taken up in the above buffer and homogenized with a Potter homogenizer. The membranes were then solubilized by adding dodecyl-maltoside (DM), at the final concentration of 0.2% (weight/vol) and a detergent/protein ratio of 0.1, and NaCl at a final concentration of 500 mM. The suspension was stirred and incubated in ice for 30 min and then centrifuged (60 min, 120 000×g).

The purification of the enzyme was carried out by medium pressure affinity chromatography on a nickel column (HiTrap chelating column 5 ml, Amersham Biosciences, Uppsala), at 4° C., by means of a chromatography system (Äktå FPLC, Amersham Biosciences, Uppsala). The column was first pre-equilibrated with 50 mM potassium phosphate buffer (pH 7.5) containing 500 mM of NaCl, 0.2% of DM and 20 mM of imidazole. After the sample had been loaded, the column was rinsed with the above solution without imidazole (solution A) in order to remove all the unbound proteins. The column was finally eluted with an increasing concentration of a solution containing 250 mM of imidazole (solution B). Fractions of 5 ml were collected at the various proportions of concentrated imidazole solution (10%, 15%, 50%, 100%).

A protein peak detected by fluorescence appeared on the chromatogram for a concentration of 125 mM of imidazole (FIG. 3A). The protein content of the fractions collected (26-29) was analyzed by 13% acrylamide gel electrophoresis under denaturing conditions (SDS-PAGE) (FIG. 3B). For comparison, the samples corresponding to the starting total fraction (T) and also to the soluble (S) and membrane (M) fractions were also analyzed.

The proteins were then transferred onto a nitrocellulose membrane and labeled by immunoblotting with a monoclonal primary antibody (Sigma) directed against a polyhistidine sequence, for 1 h, and then a secondary antibody, directed against mouse IgGs, coupled to alkaline phosphatase, also for 1 h.

In FIG. 3B (29), the presence of a strong band labeled with the antibody, the molecular weight of which is less than 50 kDa, which corresponds to the expected size of the protein (44 kDa), is observed. This protein is found in the membrane fraction (M) and not in the soluble fraction (S).

Fraction 29 was concentrated by ultrafiltration to a volume of 900 µl. A volume of 220 µl of pure glycerol was added and the enzyme was stored at −80° C. The concentration of the enzyme was evaluated on an SDS-PAGE gel by comparison with a standard range of BSA (bovine serum albumin).

III—Characterization of the Enzyme

1—Analysis of the Coenzyme

The nature of the coenzyme was determined by fluorimetry as described by FANG and BEATTIE (Biochem. 41: 3065-3072, 2002). The purified enzyme was brought to boiling for 3 to 4 min and then centrifuged.

The supernatant was analyzed by HPLC using a Supelcosil LC-DP column of 150×4.6 mm (Supelco). The mobile phase is composed of 80% of 0.1% TFA in water and of 20% of 0.1% TFA in acetonitrile at 40%. The flow rate in the column at ambient temperature is 1 ml/min. The excitation and emission wavelengths of the fluorescence detector were regulated respectively at 450 and 525 nm. FAD (Sigma) and FMN (Sigma) standards were analyzed in parallel.

Figure 4:
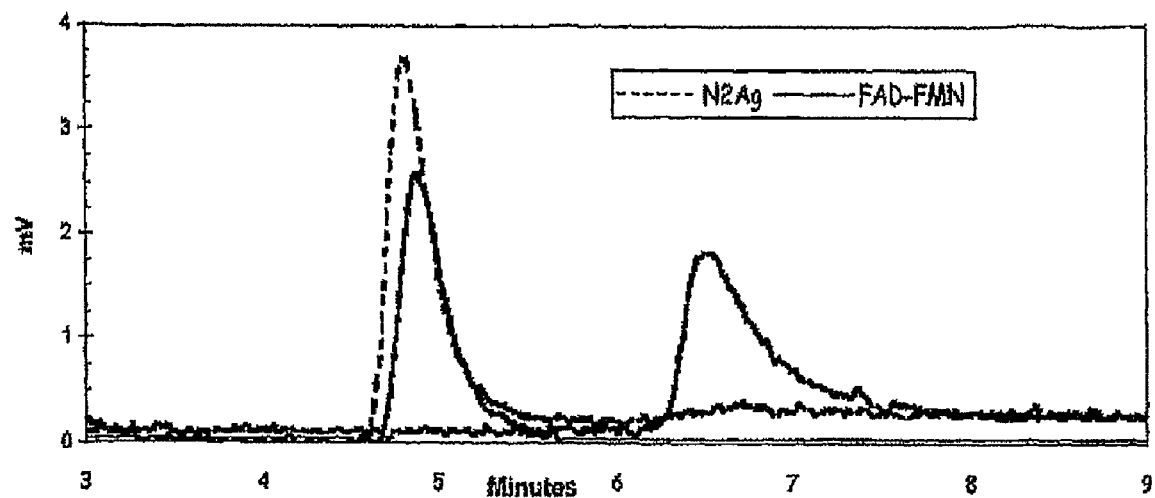
FIG. 4 is a chromatogram trace of the coenzyme of Example 1 (III).

It can be seen, in FIG. 4, that the emission peak of the enzyme sample (N2Ag) corresponds exactly to the peak of the FAD standard.

These results show that the cofactor of the *Agrobacterium tumefaciens* NDH-II is FAD.

2—Measurement of the Enzymatic Activity on Bacterial Membranes

In the next experiment, the capacity of this enzyme to transport electrons to the respiratory chain of *E. coli* was determined.

The activity of the *Agrobacterium tumefaciens* NDH-II was assayed using membranes from an *E. coli* strain deficient in NDH-I and NDH-II (ndh::tet; nuoB::nptl).

The *E. coli* strain ANN0222 (parent strain AN398; WALLACE and YOUNG, Biochim. Biophys. Acta. 461: 84-100, 1977) was cultured in 50 ml of LB-tetracycline until the end of the exponential growth phase (OD=1). The cells were then collected by centrifugation (15 min, 3200×g) and washed twice with 10 ml of solution containing 200 mM Tris-Cl, pH 8, 2.5 mM EDTA and 0.2 mM PMSF. They were then ruptured by passing them twice through a French press at the pressure of 16 000 psi.

The membrane fraction was recovered by centrifugation (30 min, 48 500×g) and resuspended in 200 µl of analysis buffer (50 mM of phosphate buffer, pH 7.5, and 150 mM NaCl).

The $O_2$ consumption of the *E. coli* ANN0222 membranes was measured by means of a Clark electrode (DW2/2, Hansatech, King's Lynn, England). After addition of the purified enzyme, this method made it possible to determine its specific activity.

The reaction mixture containing 10 µl of bacterial membranes and 1.5 µl of purified enzyme (conserved at 1 mg/ml) was preincubated for 10 min in ice before being diluted in 990 µl of analysis buffer (50 mM of phosphate buffer, pH 7.5, and 150 mM NaCl) and introduced by pipetting into the analytical chamber of the electrode. The reaction was followed at 25° C. in the presence of increasing concentrations of NADH or NADPH as electron donors.

Figure 5:
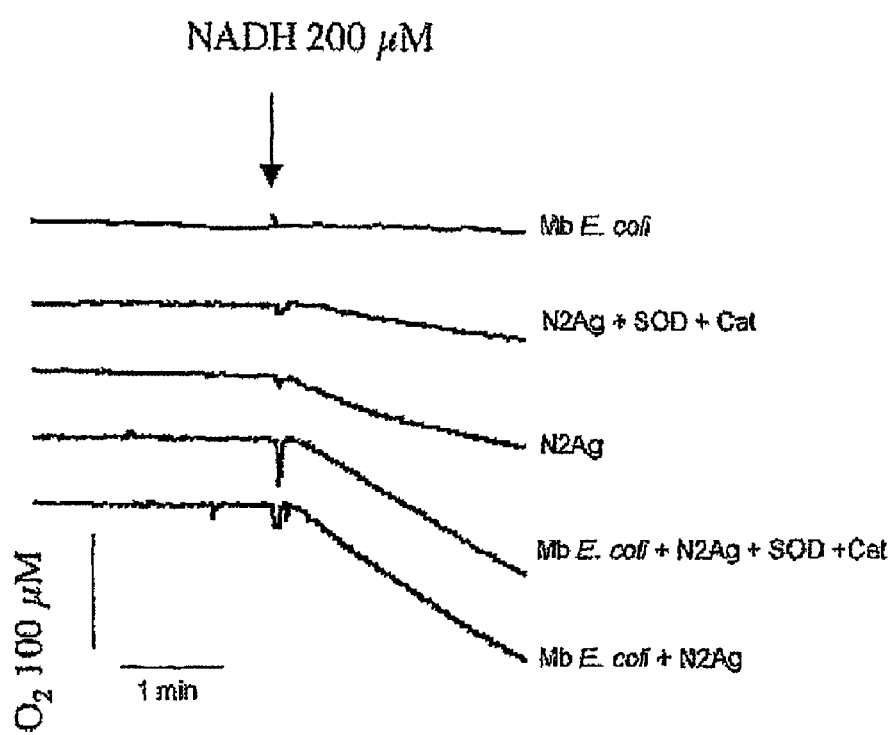
FIG. 5 illustrates the oxygen update activity of the enzyme of Example 1.

By following the reaction in the absence of bacterial membranes, it was observed that the enzyme exhibits a direct $O_2$ uptake activity. The latter, greatly reduced in the presence of SOD and catalase, is linked to the formation of active oxygen species (FIG. 5).

In order to measure only the membrane-linked respiratory oxidase activity, catalase (1000 U/ml) and superoxide dismutase (SOD) (500 U/ml) were added to the reaction mixture. The inhibitory effect of diphenylene iodonium (DPI) was quantified after 10 min of incubation in ice in the presence of the enzyme-membrane mixture. The inhibition kinetics were determined in the presence of 200 µM of NADH or of 2 mM of NADPH.

Figure 6:
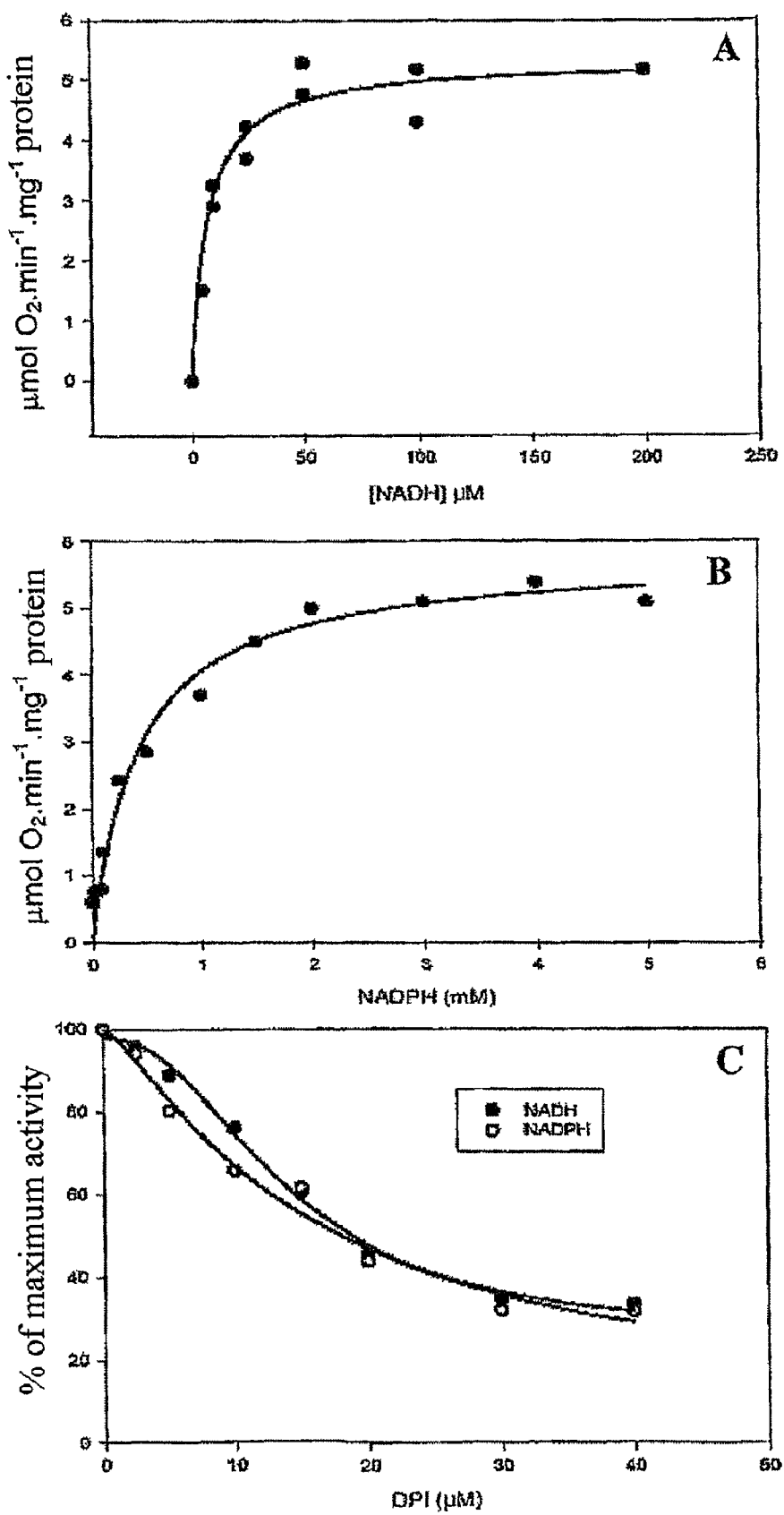
FIG. 6 is a series of graphs illustrating the affinity of the enzyme of Example 1 for NADH, NADPH and DPI.

The maximum activity of the *Agrobacterium* NDH-II (Vmax=5 µmol $O_2 \cdot min^{-1} \cdot mg^{-1}$ protein) is within the order of magnitude of the other NDH-IIs described in the literature. A physiological pH, this enzyme has a strong affinity for NADH (Km=10 µM) (FIG. 6A), but also a not insignificant affinity for NADPH (Km=50 µM) (FIG. 6B), which is rare for a bacterial enzyme. This characteristic is advantageous in terms of making this enzyme function in chloroplasts, since this cellular compartment contains an abundance of NADPH. The enzyme is clearly affected by the conventional NDH-II inhibitors, and in particular DPI, with an $I_{50}$ of 10 µM (FIG. 6C).

EXAMPLE 2

Demonstration of the Reduction of *Chlamydomonas reinhardtii* Plastoquinones by the *Agrobacterium* NDH-II The plastoquinone-reducing activity by the *Agrobacterium* NDH-II was analyzed by measuring chlorophyll fluorescence. In the presence of a weak nonactinic illumination, the measurement of chlorophyll fluorescence provides an indication of the plastoquinone redox state.

I—Preparation of Thylakoid Membranes

A culture of 200 ml of *Chlamydomonas reinhardtii* (wild-type 137c) was sampled in the exponential growth phase (approximately $5 \times 10^6$ cells·ml$^{-1}$), and then centrifuged (5 min, 1000×g). The cells were washed in 35 mM HEPES-NaOH buffer (pH 7.2), resuspended in 10 ml of lysis buffer (50 mM tricine-NaOH, pH 8, 10 mM NaCl, 5 mM MgCl$_2$, 1% BSA, 1 mM benzamidine and 1 mM PMSF) and stored in the cold and in the dark for the following steps.

The suspension was passed through a French press twice, at 2000 psi. The lysate was first centrifuged (5 min, 4° C., 500×g) in order to remove the unlysed cells, and the thylakoid membranes were then pelleted at 10 000×g for 10 min and resuspended in 250 to 500 µl of analysis buffer (50 mM tricine-NaOH, pH 7.2, 10 mM NaCl and 5 mM MgCl$_2$).

II—Plastoquinone Reduction

The photosystem II fluorescence was measured using a modulated light fluorimeter (PAM 101-103, Walz, Effeltrich, Germany).

A nonactinic modulated light (650 nm, 1.6 kHz) was used to determine the level of chlorophyll fluorescence $F_0$. The maximum level of the chlorophyll fluorescence $F_m$ was measured under a saturating flash of 1 second (approximately 1000 µmol photons·m$^{-2}$·s$^{-1}$). In order to prevent reoxidation of the plastoquinones, the experiments were carried out under anaerobic conditions by adding, to the reaction mixture, glucose (20 mM), glucose oxidase (2 mg·ml$^{-1}$) and catalase (1000 units·ml$^{-1}$).

The thylakoid membranes were incubated with or without the NDH-II (1.5 µg·ml$^{-1}$ final concentration) for 10 min in ice and the rate of reduction of the plastoquinones was compared before and after the addition of 200 µM of NADH. The results are given in FIG. 7 (NDH2Ag=presence of the *Agrobacterium* NDH-II; control=presence of natural enzyme alone; DPI=inhibitory effect of DPI).

Figure 7:
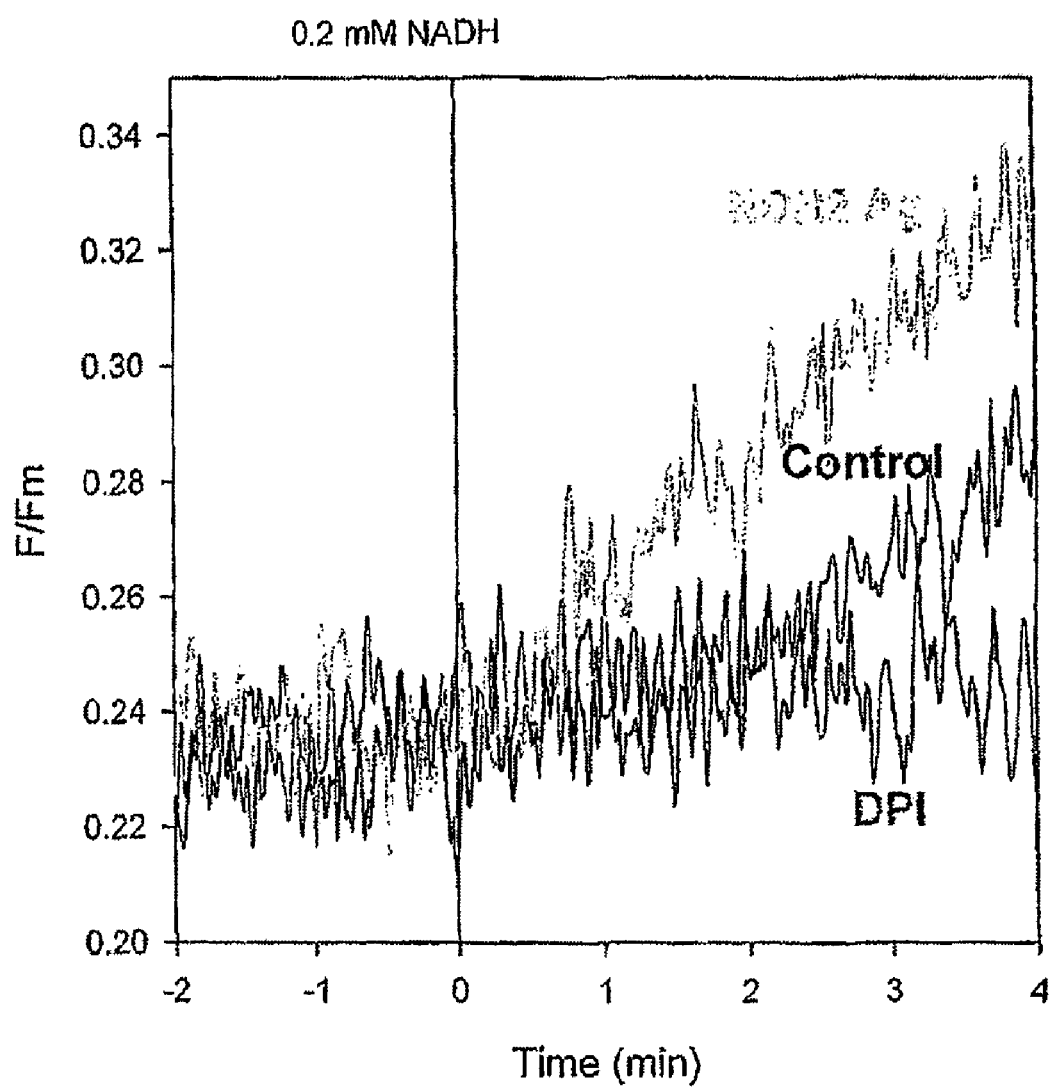
FIG. 7 is a graph showing the plastoquinone-reducing activity by the *Agrobacterium* NDH-II of Example 2 measured by chlorophyll fluorescence.

FIG. 7 shows that the fluorescence of the chlorophyll measured on thylakoid membranes from *Chlamydomonas* increases after the addition of NADH. This increase corresponds to the nonphotochemical reduction of the PQs by the alga's natural enzyme. However, in the presence of the purified *Agrobacterium* NDH-II (NHD2Ag), the increase in fluorescence is more rapid and more intense. The plastoquinone reduction is therefore greater than that performed by the natural enzyme alone (control). This demonstrates the capacity of the *Agrobacterium* NDH-II to interact with the photosynthetic electron transport chain.

In order to quantify this effect of the *Agrobacterium* NDH-II on the electron flow from NAD(P)H to the acceptors of PSI, oxygen consumption measurements were carried out in the presence of methyl viologen (an acceptor of PSI), of DCMU (an inhibitor of PSII) and of an NADH (200 µM) or NADPH (2 mM) electron donor.

The *Chlamydomonas* thylakoids (50 µl, corresponding to 85 µg·ml$^{-1}$ of chlorophyll) are placed in a Clark electrode containing 900 µl of analysis buffer (50 mM tricine-NaOH, pH 7.2, 10 mM NaCl and 5 mM MgCl$_2$, 25 µM DCMU, 50 µM methyl viologen, SOD (500 U·ml$^{-1}$), catalase (1000 U·ml$^{-1}$), 4 µM of myxothiazol and 800 µM of SHAM (salicylhydroxamic acid). The latter two compounds are added in order to inhibit respiratory $O_2$ uptake.

Under these conditions, the fraction of the photo-induced oxygen uptake sensitive to DNP-INT (2-iodo-6-isopropyl-3-methyl-2',4,4'-trinitrodiphenyl ether; 10 µM), an inhibitor of cytochrome $b_6f$, is proportional to the electron transport between the NAD(P)H and the photosynthetic chain.

The addition of 1.5 µg of purified *Agrobacterium tumefaciens* NDH-II stimulates this electron transport from 20 to 45 nmol·min$^{-1}$·mg$^{-1}$ chlorophyll when NADPH is used as donor, and from 21 to 67 nmol·min$^{-1}$·mg$^{-1}$ chlorophyll when NADH is used as donor.

This experiment therefore makes it possible to quantify the stimulation of the electron transport between NADPH (or NADH) and the thylakoid plastoquinones due to the addition of *Agrobacterium tumefaciens* NDH-II. The stimulation is by a factor of approximately 2 in the case of NADPH and by a factor of approximately 3 in the case of NADH.

These in vitro results make it possible to suppose that a heterologous expression of an NDH-II in *Chlamydomonas reinhardtii* (and, more generally, in any alga capable of producing hydrogen), whether it is chloroplastic, or nuclear with targeting to the chloroplast, can increase the intrachloroplast plastoquinone reductase activity and the associated production of $H_2$.

EXAMPLE 3

Transformation of *Chlamydomonas reinhardtii* with the Sequence Encoding the *Agrobacterium tumefaciens* NDH-II I—Construction of the Plasmid pSADN2Ag The Agtundh2 gene was amplified by PCR from the genome of *A. tumefaciens* (strain C58) using the following primers:

```
ndhAgTu.F
5'-TCCCCCGGGATGCAAGAACATCATGTT-3'     (SEQ ID NO: 12)
(Tm 66.5° C.)

and ndhAgTu.R
5'-CCGCAATTGTCAGGCCTCGTCCTTCAG-3'     (SEQ ID NO: 13)
(Tm 69.5° C.)
``` and under the following conditions:
 Reaction Mix:
 Specific reaction buffer containing 1.5 mM MgCl$_2$
 Primers at 0.5 µM final concentration
 dNTP mix at 200 µM final concentration
 300 ng of DNA
 1.5 units of Expand High Fidelity Taq polymerase (Roche)
 Amplification Conditions:
 3 min at 95° C.+1 min at 80° C.: 1 cycle
 1 min at 95° C.+1 min at 60° C.+2 min at 72° C.: 30 cycles
 6 minutes at 72° C.: 1 cycle.
 The amplification product was digested with SmaI/mfeI.
 The plasmid pGEND2 (FISHER and ROCHAIX, Mol. Genet. Genomics 265: 888-894, 2001) was digested with NaeI/EcoRI, in order to excise the sequence encoding the PsaD protein, with the exception of the chloroplast targeting peptide. The excised fragment was replaced with the SmaI/mfeI fragment obtained from the N2Ag gene amplification product.

The resulting plasmid, called pSADN2Ag, therefore contains the sequence encoding the *Agrobacterium tumefaciens* NDH-II, under the control of the promoter of the psaD gene, and as a translational fusion with the chloroplast targeting peptide of the PsaD protein.

II—Transformation of *Chlamydomonas reinhardtii*

A *Chlamydomonas reinhardtii* mutant deficient in arginosuccinate lyase (CC-2852 arg7 cw15 mt+, *Chlamydomonas* Center, Duke University, Durham, USA), and therefore auxotrophic for arginine, was used. The algae are placed in culture on a TAP medium, in a volume of 200 ml (HARRIS, The *Chlamydomonas sourcebook*, Academic Press, San Diego, 1989), supplemented with 100 mg/l of arginine, with shaking, at a temperature of 25° C., and with continuous light of approximately 35 µmol photons·$m^{-2}·s^{-1}$.

At the end of the exponential phase (concentration of approximately $10^7$ cells/ml), the algae are concentrated by centrifugation and taken up in TAP so as to obtain a suspension at $3 \times 10^8$ cells/ml.

The plasmid PSADN2Ag is used with the plasmid p389 (*Chlamydomonas* Center, Duke University, Durham, USA; http://www.chlamy.org/strains/plasmids.html) composed of a nuclear DNA fragment of *Chlamydomonas*, 7.1 kb in size, including the Arg7 gene, and cloned into BamHI in the vector pBR329, in order to cotransform the algae.

300 mg of glass beads, 0.5 mm (Sigma), 10 µl of plasmid PSADN2Ag (=1 µg), 2 µl of plasmid p389 (=0.2 µg) and 350 µl of algal suspension (=approximately $10^8$ cells) are mixed in a tube. The tube is vortexed at maximum speed for 15 seconds. 650 µl of TAP are then added and, after homogenization, the suspension is used to inoculate two Petri dishes (450 µl on each dish) containing arginine-free TAP medium (agar 15 g/l).

After incubation for 10 days in continuous light (35 µmol·$m^{-2}·s^{-1}$) and at 25° C., the algae are subcultured on the same medium. After 2 subculturings, the transformants that have grown without arginine are harvested.

The transformants having integrated the N2Ag gene are selected by detecting the presence of this gene by PCR.

The colonies are lysed according to the following protocol:

Each colony is taken up in 100 µl of sterile water (milliQ® filtration). 5 µl of 10×PCR buffer, 1 µl of 0.01% SDS, 1 µl of 200 mM DTT, 3 µl of cells and 39 µl of $H_2O$ are mixed in a 1.5 ml tube.

5 freezing/thawing cycles (between liquid nitrogen and a water bath at 55° C.) are carried out.

2 µl of proteinase K at 10 µg/ml are added and the mixture is incubated for 1 h at 55° C.

The proteinase K is inactivated by treatment at 95° C. for 5 minutes.

The PCR is carried out using the ndhAgTu.F and ndhAg-Tu.R primers, and under the following conditions:

Reaction Mix:
For a final volume of 25 µl
2.5 µl of 10× buffer
2 µl of dNTP mix
1.25 µl of each primer
2.5 µl of 10×BSA
3 µl of cell lysate
0.3 µl of Taq polymerase (Qiagen)
12.2 µl $H_2O$ Amplification Conditions:
3 min at 95° C.+1 min at 80° C.: 1 cycle
1 min at 95° C.+1 min at 60° C.+2 min at 72° C.: 30 cycles
6 minutes at 72° C.: 1 cycle.

A positive control was carried out by replacing the *Chlamydomonas* genomic DNA with the plasmid that had been used for the transformation.

The amplification products were analyzed by 1% agarose gel migration and visualized after staining the gel with ethydium bromide (FIG. 8). A molecular weight marker was loaded in parallel on the gel in order to estimate the size of the amplification products obtained.

The transformants that have integrated the NDH-II gene show a band of approximately 1.2 kb that is also observed on the positive control. The proportion of cotransformants (=that have integrated the two plasmids) is approximately 50%.

III—Expression of NDH-II

The expression of the *Agrobacterium* NDH-II gene was verified by RT-PCR in 6 cotransformants. The total RNA is extracted from 25 ml of exponential-phase culture with the RNeasy® kit, according to the supplier's indications (Qiagen). The cDNAs are prepared using the Omniscript® kit, according to the protocol recommended by the supplier (Quiagen), adjusting the volume of the various RNAs so as to obtain 2 µg in each reaction.

The PCR is carried out using the ndhAgTu.F and ndhAg-Tu.R primers, and under the following conditions:

Reaction Mix:
Specific reaction buffer containing 1.5 mM $MgCl_2$
Primers at 0.5 µM final concentration
dNTP mix at 200 µM final concentration
300 ng of cDNA
1.5 units of Expand High Fidelity Taq polymerase (Roche)
Amplification Conditions:
3 min at 95° C.+1 min at 80° C.: 1 cycle
1 min at 95° C.+1 min at 60° C.+2 min at 72° C.: 30 cycles
6 minutes at 72° C.: 1 cycle.

A negative control was carried out in order to verify that the amplicons observed do not come from an amplification of the nuclear DNA persisting after the digestion step included in the RNA extraction protocol. For this control, the 300 ng of cDNA obtained after the reverse transcriptase step are replaced with 5 µl of the RNA solution preceding this step.

In order to control the efficiency of the extraction protocol and also the level of expression of the NDH-II, the cDNA of actin 1, which is a protein expressed constitutively and in large amounts, was amplified in parallel.

The amplification products were analyzed by 1% agarose gel migration and visualized by staining the gel with ethydium bromide (FIG. 9). A molecular weight marker was loaded in parallel on the gel in order to estimate the size of the amplification products obtained.

The cotransformants expressing the NDH-II gene show a band of approximately 1.2 kb corresponding to the size of the insert. The negative control does not show any band, which means that the RNA preparations were not contaminated with genomic DNA, whereas it clearly shows an actin amplification product. All the cotransformants tested express the NDH-II gene at different levels, but at the same order of magnitude as that of actin.

EXAMPLE 4

Functional Complementation of an NDH-Deficient E. Coli Strain

I—Complementation-Growth Test

The functionality of the Agtundh2 protein in vivo in a heterologous host was tested by determining its capacity to restore the growth of a mutant E. coli strain, ANN.0222, deficient in NDH-1 and in NDH-2. This strain grows normally on LB medium, but is incapable of growing on minimum medium M9 supplemented with mannitol as the sole carbon source.

The E. coli strain ANN.0222 was chemically transformed ($CaCl_2$) with the plasmid pSDN2Ag6H. The transformants were selected on LB agar medium (supplemented with 1% tryptone, 0.5% of yeast extract and 0.5% NaCl, pH 7) containing ampicillin (100 µg/ml). The transformants and the strain of origin were cultured until the middle of the exponential phase at 37° C. in liquid LB medium containing ampicillin (100 µg/ml). The cells were rinsed with sterile M9 medium, supplemented with mannitol as the sole carbon source (1× M9 salts, $2 \times 10^{-3}$ M $MgSO_4$, $10^{-4}$ M $CaCl_2$, 0.4% mannitol). The cells were then diluted in M9 medium/mannitol and inoculated on a solid M9/mannitol/agar medium containing ampicillin and various concentrations of IPTG. The Petri dishes were incubated at 37° C. for 2 days. As a control, the same cells were inoculated in parallel on dishes containing LB agar medium containing ampicillin and various concentrations of IPTG, and then incubated at 37° C. overnight.

The results are illustrated in FIG. 10A, which represents the formation of colonies on rich medium (LB) and on minimal medium supplemented with mannitol (M9+mannitol) for the ANN0222 strain and the transformant which expresses Agtundh2 (noted AtuNdh2 on the figure). The IPTG concentrations are indicated above each corresponding lane.

The growth of the nontransformed mutant strains is considerably limited on minimal medium, whether in the absence or presence of IPTG (0.1 mM). On the other hand, the growth, on minimal medium, of the strain expressing Agtundh2 was restored after induction with 0.1 mM IPTG. A partial complementation of the mutant was observed even in the absence of IPTG, which suggests a certain level of IPTG-independent expression of the protein.

II—Membrane NADH Dehydrogenase Activity

Two batches of E. coli ANN.0222 membrane fractions were prepared, from a culture of the control strain on LB medium and from a culture of the strain having incorporated the plasmid pSDN2Ag6H, cultured on LB medium in the presence of 0.1 mM IPTG. The cultures were carried out until an optical density of 1 at 600 nm was obtained. The cells were collected by centrifugation (15 min, 3200×g), rinsed twice, and resuspended in 10 ml of buffer A (200 mM Tris-Cl, pH 8, 2.5 mM EDTA and 0.2 mM PMSF; (30)). The cells were then ruptured by passing them through a French press twice, at 16 000 psi. The membrane fraction, collected by centrifugation (30 min, 4° C., 48,500×g), was taken up in 200 µl of buffer B (50 mM phosphate buffer, pH 7.5 and 150 mM NaCl). The $O_2$ uptake was measured using a Clark electrode (DW2/2, Hansatech, King's Lynn, England), on aliquots of 2 µl of these membrane fractions, diluted in 1 ml of buffer A, at 25° C. and in the presence of NADH.

The results are illustrated by FIG. 10B, which represents the $O_2$ uptake, in the presence of NADH, of E. coli ANN0222 membranes prepared from the reference strain (control) and from the strain expressing Agtundh2.

Although no $O_2$ uptake activity is detected in the membranes from the control strain in response to the addition of NADH, a considerable $O_2$ uptake is, on the other hand, detected under the same conditions in the membranes of the strain transformed with pSDN2Ag6H (FIG. 10B). When expressed in E. coli membranes, Agtundh2 is capable of oxidizing NADH and NADPH with maximum rates of the same order, but with a much greater affinity for NADH.

III—Expression of the Protein

The expression of the Agtundh2 protein in the transformed ANN.0222 strain was confirmed by immunodetection.

A rabbit serum was produced against the purified Agtundh2 protein (Agro-Bio, Villeny, France). The soluble and membrane protein fractions were extracted as indicated above. These protein fractions, and also aliquots of the purified Agtundh2 protein, were loaded onto a 10% SDS-PAGE gel and subjected to electrophoresis, and then blotted onto nitrocellulose membranes. The nitrocellulose membranes were then incubated for 30 minutes in milk (3% powdered skimmed milk in water to which 0.1% TBST was added), and then rinsed with 0.1% TBST and then again incubated for 1 h 30 with the anti-Agtundh2 antibody diluted to 1/10 000th. The membranes were then rinsed three times for 10 minutes with 0.1% TBST and then incubated for 1 h with an alkaline phosphatase-conjugated anti-rabbit secondary antibody diluted to 1/10 000th. The reaction was detected according to the protocol recommended by the supplier (Sigma).

Figure 11:
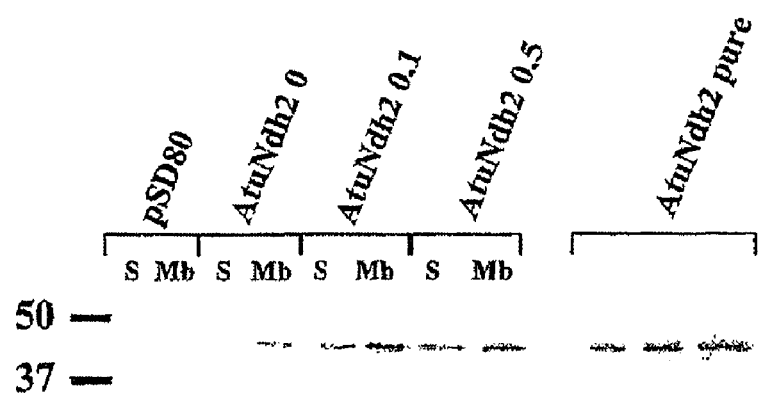
FIG. 11 is a gel electrophoresis of the Agtundh2 protein fractions of Example 4.

The results are illustrated in FIG. 11: left panel: immunodetection on soluble (S) and membrane (Mb) protein fractions of the E. coli strain ANN0222, transformed either with the "empty" pSD80 vector, or with the construct carrying Agtundh2, and exposed to 0, 0.1 or 0.5 mM of IPTG. The loading of the gel ultimately corresponded to a 1/400th dilution of the soluble and membrane fractions of 50 ml of culture harvested at $OD_{600}=1$ (i.e. 2.5 µg of proteins on the lanes corresponding to the membrane fractions and 30 µg of proteins on those corresponding to the soluble fractions). Right panel: immunodetection of purified Agtundh2, at 0.1, 0.2 and 0.3 µg/lane from left to right.

The majority of the protein was found in the membrane fractions, a minor proportion being detected in the soluble proteins. A significant expression of Agtundh2 was detected even in the absence of IPTG, which is in agreement with the partial complementation observed under these conditions (cf. FIG. 10A).

To determine the catalytic efficiency of Agtundh2 expressed in E. coli, the specific activity was estimated from the amounts determined by Western blotting.

On the basis of the relative intensities of the signals obtained for the purified Agtundh2 protein and for the membrane fractions, the amount of Agtundh2 protein in the experiments illustrated by FIG. 10B was estimated at 0.6 µg protein. The maximum $O_2$ uptakes under these conditions are thus estimated at $13.2/0.6=22$ nmol $O_2$ $min^{-1} \cdot µg^{-1}$ protein, i.e. 44 nmol NADH $min^{-1} \cdot µg^{-1}$ protein.

EXAMPLE 5

Modification of the Relative Specificity of Agtundh2 for NADH and NADPH

I—Amplification of the Agtundh2 Gene

The Agtundh2 gene was amplified from the plasmid pSDN2Ag6H using the following pair of primers:

```
*Sense: N2Ag.NcoI
ATGGAACATCATGTTGTCGTC          (SEQ ID NO: 14)
```

The NcoI (in italics) restriction site was inserted into the primer in such a way as to overlap the start codon of the gene (in bold) and by modifying the fourth base of the sequence (C becomes G).

```
*Antisense: N2Ag.XbaI
CCGTCTAGATCAGGCCTCGTCCTTCAGCGT    (SEQ ID NO: 15)
```

The XbaI (in italics) restriction site was inserted into the antisense primer downstream of the stop codon of the gene (in bold).

The amplification was carried out under the following conditions:
1—Reaction Mix:
1× specific reaction buffer
1.5 µM MgSO$_4$ final concentration
Primers at 0.5 µM final concentration
dNTP mix at 200 µM final concentration
200 ng of DNA
1 unit of Pfx platinum (Invitrogen)
2—Amplification Conditions:
2 min at 94° C.: 1 cycle
30 sec at 94° C.+1 min at 55° C.+3 min at 68° C.: 25 cycles
10 min at 68° C.: 1 cycle.

II—Introduction of the E201Q Mutation into the Sequence of the Agtundh2 Gene:

The E201Q mutation of the Agtundh2 gene was introduced into the sequence of the gene by the "PCR fusion" site-directed mutagenesis technique. The fragments corresponding to the first amplification step were obtained using the plasmid pSDN2Ag6H as template. The pairs of primers used are the following:

```
*Sense: N2Ag.NcoI;
*Antisense: N2Ag.E201Q.R
AGGGCCGGCCTGCACAAGCAA.         (SEQ ID NO: 16)
```

The N2Ag.E201Q.R primer makes it possible to introduce the E201Q mutation (in bold).

These two primers make it possible to obtain the 5' fragment containing the E201Q mutation.

```
*Antisense: N2Ag.XbaI;
*Sense: N2Ag.E201Q.F
TTGCTTGTGCAGGCCGGCCCT.         (SEQ ID NO: 17)
```

The N2Ag.E201Q.F primer makes it possible to introduce the E201Q mutation (in bold).

These two primers make is possible to obtain the 3' fragment containing the E201Q mutation.

Reaction Mix:
1× specific reaction buffer
1.5 µM MgSO$_4$ final concentration
Primers at 0.5 µM final concentration
dNTP mix at 200 µM final concentration
200 ng of DNA
1 unit of platinum Pfx (Invitrogen)
Amplification Conditions:
2 min at 94° C.: 1 cycle
30 sec at 94° C.+1 min at 55° C.+3 min at 68° C.: 25 cycles
10 min at 68° C.: 1 cycle.

The two amplification fragments contain the mutation of interest introduced by virtue of the N2Ag.E201Q.F and N2Ag.E201Q.R primers.

The second amplification step is carried out by mixing the two amplification fragments obtained in the preceding step. These two fragments were hybridized by virtue of their common sequence (TTGCTTGTGCAGGCCGGCCCT) (SEQ ID NO: 17) and will thus constitute the template. The amplification is carried out using the two primers N2Ag.NcoI and N2Ag.XbaI, under the following conditions:

Reaction Mix:
1× specific reaction buffer
1.5 µM MgSO$_4$ final concentration
Primers at 0.5 µM final concentration
dNTP mix at 200 µM final concentration
200 ng of N2Ag.NcoI/N2Ag.E201Q.R fragment
200 ng of N2Ag.XbaI/N2Ag.E201Q.F fragment
1 unit of platinum Pfx (Invitrogen)
Amplification Conditions:
2 min at 94° C.: 1 cycle
30 sec at 94° C.+1 min at 55° C.+6 min at 68° C.: 30 cycles
10 min at 68° C.: 1 cycle.

III—Cloning of the Constructs

The amplification product was digested with NcoI and XbaI (New England Biolabs, protocol recommended by the supplier) and introduced by ligation (T4 DNA ligase from New England Biolabs, protocol recommended by the supplier) into the vector pBAD24 digested with NcoI and XbaI. This vector carries an ampicillin-resistance cassette, and an arabinose-inducible pBAD-type promoter. The amplification products were then introduced by electroporation into *E. coli* dH10β. The ampicillin-resistant transformants were selected and the presence of the insert was verified by extraction of the plasmid DNA and digestion with NcoI and HindIII. The two constructs were then verified by sequencing using primers internal to the Agtundh2 gene (N2Ag.E201Q.F; N2Ag.NcoI; N2Ag.E201Q.R; N2Ag.XbaI).

The sequencing showed that the desired mutation (E201Q) had indeed been introduced. The plasmid was called E201Qc1.

IV—Activity of the Modified Protein

The affinity of the modified protein for NADH and NADPH was determined.

Figure 12:
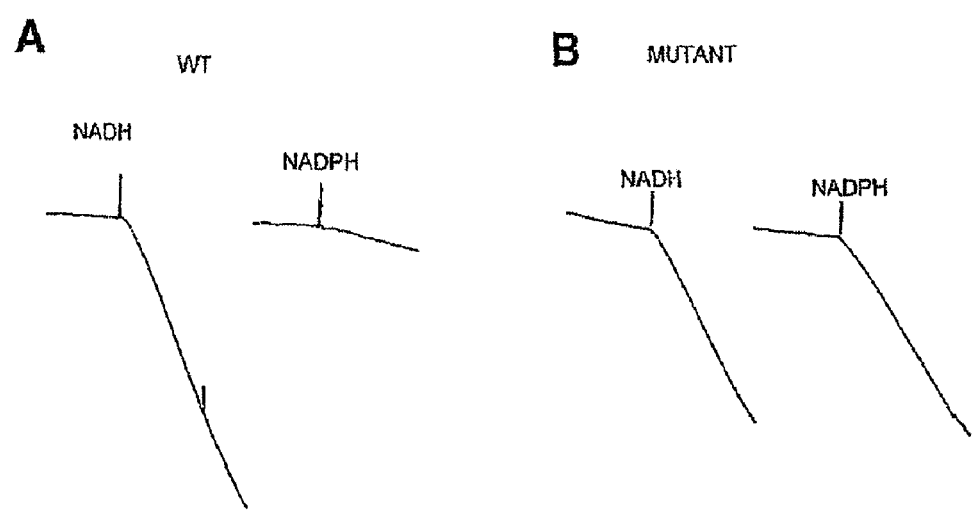
FIG. 12 illustrates the affinity of the modified protein of Example 5 for NADH and NADPH.

The results are illustrated in FIG. 12. While the wild-type protein (A) exhibits a clearly greater activity with 200 µM NADH compared with that recorded with 200 µM NADPH, the modified protein (B) exhibits a comparable activity for the two substrates.

EXAMPLE 6

Identification of a Chloroplast-Located NDH2 from *Chlamydomonas reinhardtii*

I—Amplification of the Gene

The total RNA was isolated from cultures of *C. reinhardtii* on TAP medium (taken between 1×10$^6$ and 1×10$^7$ cells/ml), using the QIAGEN RNeasy® Plant Mini Kit, in accordance with the supplier's instructions. The cDNA synthesis was carried out using the Omniscript™ Reverse Transcriptase system (QIAGEN) with an oligo-dT primer. The reaction products were amplified by PCR with the turbo pfu polymerase (Stratagene) in an OmniGene Hybrid thermocycler.

cDNA Amplification Conditions:
Denaturation at 94° C.: 5 min
30 s at 94° C., 40 s at 72° C. and 2 min at 72° C.: 5 cycles
30 s at 94° C., 40 s at 68° C. and 2 min at 72° C.: 5 cycles
30 s at 94° C., 40 s at 65° C. and 2 min at 72° C.: 5 cycles
30 s at 94° C., 40 s at 62° C. and 2 min at 72° C.: 15 cycles
Extension at 72° C.: 5 min.
The primers used for the amplification of N2Cr2 are:

5'-ATGCATAGCCTTGATGGCCAAAAC-3'  (SEQ ID NO: 18)

and

5'-TCACACTCGCGAGATGTCGCG-3'.  (SEQ ID NO: 19)

These two primers made it possible to amplify a cDNA (1662 bp) by RT-PCR. The new sequence thus identified was named N2Cr2. The cDNA corresponding to N2Cr2 encodes a polypeptide of 533 amino acids with a predicted mass of 60.5 kDa.

In comparing the sequence of this cDNA with the available genomic sequences of *C. reinhardtii*, it was noted that it in fact corresponds to a protein with a 65-amino acid truncation at its N-terminal end.

The complete cDNA sequence of N2Cr2 is represented in the attached sequence listing under the number SEQ ID NO: 3, and the deduced polypeptide sequence under the number SEQ ID NO: 4. The cloned cDNA corresponds to nucleotides 196-1857 of the sequence SEQ ID NO: 3, and encodes a polypeptide corresponding to amino acids 67-619 of the sequence SEQ ID NO: 4.

The protein encoded by the cloned 1662 bp cDNA sequence, although truncated at its N-terminal end, encodes a protein that effectively exhibits an NADH dehydrogenase activity, and that made it possible to generate an antibody which recognizes the N2Cr2 protein in *Chlamydomonas*, as illustrated hereinafter.

II—Cloning of the Gene in pSD80

The N2Cr2 coding region of the 1662 bp cDNA sequence was amplified by PCR using primers corresponding to the N- and C-terminal parts of the sequence, extended by additional bases conferring the EcoRI and SmaI restriction sites and a 6-histidine coding sequence. The EcoRI and SmaI sites (underlined) were inserted into the forward (F) and reverse (R) primers, respectively upstream and downstream of the start and stop codons. The 6-histidine coding sequence (in italics) was inserted into the F primer downstream of the start codon of the N2Cr2 coding region. The sequences of the oligonucleotides are therefore:

*F-EcoRI:
(SEQ ID NO: 20)
5'-CGGAATTCATG*CATCATCATCATCATCAT*AGCCTTGATGGCCAA
AAC-3' and

*R-SmaI:
(SEQ ID NO: 21)
5'-TCCCCCGGGTCACACTCGCGAGATGTCGCG-3'.

The amplified cDNA was digested with EcoRI and SmaI and inserted into the pSD80 expression vector carrying carbenicillin resistance (Patel and Dunn, 1995), digested beforehand with EcoRI and SmaI. The resulting plasmid, called pSD80-N2Cr2, was verified by sequencing and then used to transform the *E. coli* strain DH10β by electroporation. The cells carrying pSD80-N2Cr2 are called DH10β(pSD80-N2Cr2). The expression of 6-His-tagged N2Cr2 was carried out in 2 liters of LB medium inoculated with 10 ml of an overnight culture of DH10β(pSD80-N2Cr2), and then placed (140 rpm) at 37° C. in the presence of carbenicillin (50 μg·ml$^{-1}$). Approximately 4 h after inoculation, the cells having reached an OD$_{600}$ nm of 0.5, the expression of 6-His-tagged N2Cr2 was initiated by adding 100 μM isopropyl-thio-β-D-galactoside (IPTG). The cells were harvested 5 h after induction, rinsed with 25 ml of LB medium (centrifugation at 4355 g, 1 min, 4° C.) and stored at −80° C.

III—Column Purification of the Tagged Protein

The isolation and the nickel-affinity purification of N2Cr2-6His were carried out according to the protocol of BJÖRKLÖF et al. (2000, mentioned above). The DH10β(pSD80-N2Cr2) cells were thawed on ice and taken up in a buffer containing 2.5 mM EDTA, 0.2 mM PMSF and 200 mM Tris-Cl, pH 8.0, at approximately 1 g per 10 ml. Lysozyme was added and the mixture was stirred for 1 h on ice. After this, the cells were ruptured by passing them through a French press twice (16 000 psi). The lysate was centrifuged at 12 000 g for 1 h and the supernatant was then collected and used for the purification of N2Cr2-6His by nickel-affinity chromatography, using a Histrap HP resin (Amersham Bioscience). The column was preequilibrated with a buffer containing 20 mM triethanolamine, 500 mM NaCl and 25 mM imidazole, pH=7.5 (buffer A). After the sample had been loaded, the column was rinsed twice with two column volumes of buffer A, and then rinsed with a similar volume of 50 mM Tris-Cl, 0.2% (w/v) dodecyl maltoside, pH=7.5 (buffer B) and, finally, with one column volume of 50 mM Tris-Cl, 0.2% (w/v) dodecyl maltoside, 10 mM CaCl$_2$, pH=7.5 (buffer C). After this "calcium wash", the column was rinsed again with three volumes of buffer B and two volumes of buffer A. N2Cr2-6His was then eluted using a gradient of imidazole prepared from 20 mM triethanolamine, 500 mM NaCl, 300 mM imidazole, pH=7.5. N2Cr2-6His was detached from the column at approximately 180 mM imidazole; the corresponding fraction was concentrated by ultrafiltration using the "Amicon Ultra 30 kDa" system (Millipore). Glycerol was added for a final concentration of 50% (v/v), and the enzyme was stored at −80° C.

IV—Production of an Antibody Against the Recombinant Protein 2 mg of protein were obtained using the purification protocol above. The purity of the protein was verified on a Coomassie-blue-stained gel and the material was used to produce a serum directed against N2Cr2, by immunization of a rabbit.

V—Cell Fractionation

Obtaining the total, mitochondrial and soluble fractions:
In order to determine the subcellular location of the protein within the *Chlamydomonas reinhardtii* cells, a cell fractionation that allowed us to separate the debris fraction, mitochondrial fraction and soluble protein fraction was carried out. For this, we used a cell-wall-less strain (CW15) that made it possible to obtain a "mild" cell fractionation by Yeda-press lysis.

400 ml of CW15 culture in the exponential growth phase of *Chlamydomonas reinhardtii* are centrifuged for 5 min at 500 g at 4° C.; the pellet is then taken up in 50 ml of 35 mM HEPES, pH 7.2, and recentrifuged for 5 min at 500 g at 4° C. The pellet taken up in 12.5 ml of lysis buffer (50 mM tricine-NaOH, 10 mM NaCl, 5 mM MgCl$_2$, pH=8) is introduced into a Yeda press in order to perform the fractionation. The cells are incubated under N$_2$ in the press for 6 min at 8 bar, and then recovered dropwise.

The sample is then centrifuged for 5 min at 500 g at 4° C. The pellet is collected and taken up in 2 ml of 1% SDS. The supernatant is centrifuged at 3220 g for 8 min at 4° C. The pellet contains thylakoids, which are not recovered since they are contaminated with mitochondrial membranes. The supernatant is centrifuged for 1 hour at 100 000 g at 4° C. The pellet contains the mitochondria and is taken up with 1 ml of 1% SDS. The supernatant constitutes the soluble fraction. The three fractions are precipitated with acetone (80% for the total and membrane proteins and 60% for the soluble fraction). A sample of each fraction is assayed using the bicinchoninic acid technique (BC Assay kit, Uptima UP40840A, INTERCHIM).

Thylakoid Extraction

In order to obtain chloroplast fractions not contaminated with mitochondrial membranes, a percoll gradient purification (COURNAC et al., J. Biol. Chem., 275, 23, 17256-17262, 2000) was carried out.

For this, 600 ml of a culture of Cw15 in the middle of the exponential growth phase are centrifuged at 500 g for 5 min at 4° C. The pellet is washed once in 50 ml of 35 mM HEPES, pH=7.2, and recentrifuged for 5 min at 500 g at 4° C. The pellet is taken up in 12.5 ml of buffer A (0.3 M sorbitol, 50 mM HEPES-KOH, pH 8.2, 2 mM EDTA, 5 mM MgCl$_2$) and introduced into the Yeda press for 3 min at 4.5 bar. The material is loaded onto a Percoll gradient (40-60%) and centrifuged for 20 min at 4000 g. The ring corresponding to the intact chloroplasts is collected and diluted in 10 times its volume of buffer A. The sample is centrifuged for 15 min at 3220 g and the pellet is taken up in 3.5 ml of 0.2% SDS and then precipitated with 80% acetone.

The sample is assayed according to the bicinchoninic acid method.

VI—Western Blotting

100 µg of each fraction are prepared by centrifuging the appropriate volume for 10 min at 10,000 rpm and resuspending the pellet in 1× loading buffer. 5 µl (i.e. 5 µg) of each fraction are loaded onto a 10% SDS-PAGE gel. As a control, approximately 0.1 µg of purified protein is also loaded onto the gel. After migration, the proteins are blotted (semi-dry blotting) onto a nitrocellulose membrane (Life sciences, BioTrace NT).

The proteins are then labeled by immunoblotting using, for the primary antibody, the antibody obtained against the recombinant protein (AGRO-BIO). The incubation lasts 1 hour at ambient temperature. The secondary antibody (anti-IgG from rabbit), coupled to a fluoro-chrome, is then added for one hour. The detection is carried out using the odyssey infrared scanner from the company LICOR.

Figure 13:
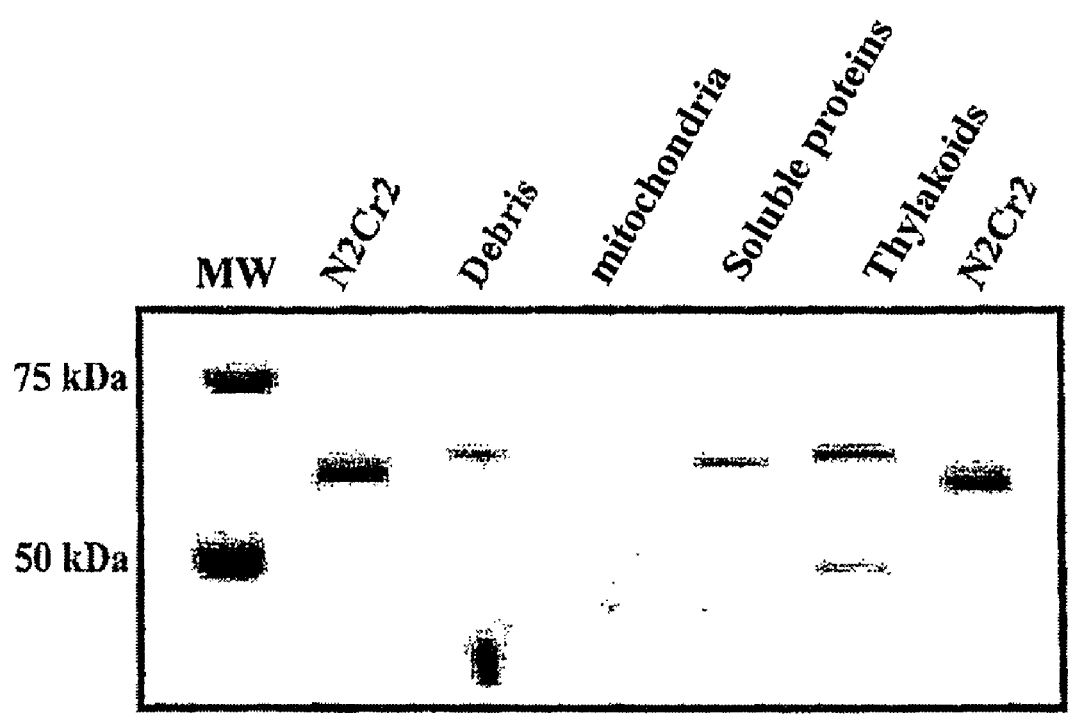
FIG. 13 is a gel electrophoresis of products of Example 6.

The results are illustrated in FIG. 13.

The band that reacts most strongly is located in the thylakoid fraction. It is slightly larger in size than the recombinant N2Cr2 produced. This difference in size is probably due to the fact that the recombinant protein is N-ter truncated compared with the predicted sequence of the mature protein in *Chlamydomonas*.

EXAMPLE 7

Cloning of Agtundh2 into the Plasmid PXX6 for Transformation if *Chlamydomonas reinhardtii*

I—Construction of the Fragment to be Cloned

In order to be able to express the Agtundh2 protein in *Chlamydomonas reinhardtii*, a product from fusion between the rbcS2 gene from *Chlamydomonas reinhardtii* and the Agtundh2 gene from *Agrobacterium tumefaciens* was created. For this, the sequence of the transit peptide of rbcS2 was placed upstream of the start codon of Agtundh2 and the sequence of the 3' UTR region of rbcS2 was placed downstream of the stop codon of Agtundh2, using the fusion PCR technique.

Amplification of the Transit Peptide of rbcS2

Firstly, the transit peptide of rbcS2 was amplified from *Chlamydomonas reinhardtii* genomic DNA using the following pair of primers:

```
*N2Ag.XhoI:
CGGCTCGAGATGGCCGCCGTCATTGCCAAG.   (SEQ ID NO: 22)
```

The restriction site of the XhoI enzyme (in italics) was introduced upstream of the start codon (in bold) of the rbcS2 gene.

```
*TP.ndh.R:
                                  (SEQ ID NO: 23)
GACGACAACATGATGTTCTTGCATCTGGTTGGCCTGAGCCGGGGCAGC.
```

The region corresponding to the sequence of the rbcS2 transit peptide is indicated in italics, and that corresponding to the Agtundh2 extension is indicated in normal characters.

Reaction Mix:
1× specific reaction buffer
1.5 µM MgSO$_4$ final concentration
Primers at 0.5 µM final concentration
dNTP mix at 200 µM final concentration
200 ng of DNA
1 unit of platinum Pfx (Invitrogen)

Amplification Conditions:
2 min at 94° C.: 1 cycle
30 sec at 94° C.+1 min at 60° C.+3 min at 68° C.: 30 cycles
10 min at 68° C.: 1 cycle Amplification of the Agtundh2 Gene The Agtundh2 gene was amplified from the plasmid pSDN2Ag6H using the following pair of primers:

```
*TP.ndh.F:
                                  (SEQ ID NO: 24)
GCTGCCCCGGCTCAGGCCAACCAGATGCAAGAACATCATGTTGTCGTC.
```

An extension corresponding to the end of the sequence of the rbcS2 transit peptide (in italics) was introduced upstream of the start codon (in bold) of Agtundh2.

```
*rbcS2.3'.R:
                                  (SEQ ID NO: 25)
GCTCAGATCAACGAGCGCCTCCATTCAGGCCTCGTCCTTCAGCGTCTC.
```

An extension corresponding to the beginning of the sequence of the 3' UTR region of rbcS2 (in italics) was introduced downstream of the stop codon of Agtundh2 (in bold).

Reaction Mix:
1× specific reaction buffer
1.5 µM MgSO$_4$ final concentration
Primers at 0.5 µM final concentration
dNTP mix at 200 µM final concentration
200 ng of DNA
1 unit of platinum Pfx (Invitrogen)
Amplification Conditions:
2 min at 94° C.: 1 cycle
30 sec at 94° C.+1 min at 55° C.+3 min at 68° C.: 30 cycles
10 min at 68° C.: 1 cycle.

Amplification of the 3' UTR Region of rbcS2:

The 3' UTR region of rbcS2 was amplified from the genomic DNA of Chlamydomonas reinhardtii using the following pair of primers:

```
rbcS2.3'.F
                                            (SEQ ID NO: 26)
GAGACGCTGAAGGACGAGGCCTGAATGGAGGCGCTCGTTGATCTGAGC N2Ag.KpnI:
                                            (SEQ ID NO: 27)
CGGGGTACCCTGCAAATGCTGTCTCCA.
```

For the rbcS2.3'.F primer, an extension corresponding to the C-terminal region of Agtundh2 (in italics) was introduced upstream of the beginning of the 3' UTR sequence of rbcS2 (in normal characters).

For the N2Ag.KpnI primer, the restriction site of the KpnI enzyme (in italics) was introduced downstream of the end of the sequence of the 3' UTR region of rbcS2 (in normal characters).

Reaction Mix:
1× specific reaction buffer
1.5 µM MgSO$_4$ final concentration
Primers at 0.5 µM final concentration
dNTP mix at 200 µM final concentration
200 ng of DNA
1 unit of platinum Pfx (Invitrogen)
Amplification Conditions:
2 min at 94° C.: 1 cycle
30 sec at 94° C.+1 min at 60° C.+3 min at 68° C.: 30 cycles
10 min at 68° C.: 1 cycle.

Amplification of a Fusion Fragment Between the rbcS2 Transit Peptide and the Agtundh2 Gene The amplification fragments corresponding to the rbcS2 transit peptide and to the Agtundh2 gene are mixed and used as a template for the amplification of the fusion fragment using the following pair of primers (see above):
N2Ag.XhoI
rbcS2.3'.R
Reaction Mix:
1× specific reaction buffer
1.5 µM MgSo$_4$ final concentration
Primers at 0.5 µM final concentration
dNTP mix at 200 µM final concentration
200 ng of rbcs 2 transit peptide fragment
200 ng of Agtundh2 gene fragment
1 unit of platinum Pfx (Invitrogen)
Amplification Conditions:
2 min at 94° C.: 1 cycle
30 sec at 94° C.+1 min at 55° C.+6 min at 68° C.: 30 cycles
10 min at 68° C.: 1 cycle.

Amplification of the Fusion Fragment Between the rbcS2 Transit Peptide, the Agtundh2 Gene and the 3' UTR Region of rbcS2:

The fusion fragment obtained above (rbcS2 transit peptide+Agtundh2 gene) is mixed with the fragment corresponding to the 3' UTR region of rbcS2 so as to act as a template for the final amplification step using the following pair of primers: N2Ag.XhoI; N2Ag.KpnI.
Reaction Mix:
1× specific reaction buffer
1.5 µM MgSO$_4$ final concentration
Primers at 0.5 µM final concentration
dNTP mix at 200 µM final concentration
200 ng of "transit peptide+Agtundh2 gene" fragment
200 ng of rbcS2 3' UTR fragment
1 unit of platinum Pfx (Invitrogen)
Amplification Conditions:
2 min at 94° C.: 1 cycle
30 sec at 94° C.+1 min at 55° C.+6 min at 68° C.: 30 cycles
10 min at 68° C.: 1 cycle.

II—Cloning the Fusion Fragment into the Plasmid pXX6

The fusion product was digested with XhoI and KpnI (New England Biolabs, protocol recommended by the supplier) and introduced by ligation (T4 DNA ligase, New England Biolabs, protocol recommended by the supplier) into the plasmid pXX6 digested beforehand with XhoI and KpnI.

The plasmid pXX6 is described by FUHRMANN M et al. (Plant Mol. Biol., 55, 6, 869-881, 2004). It carries an ampicillin-resistance cassette, a region of the strong Hsp promoter of Chlamydomonas reinhardtii that optimizes transcription of the gene placed downstream, the constitutive promoter of the rbcS2 gene from Chlamydomonas reinhardtii, and the first intron of the rbcS2 gene from Chlamydomonas reinhardtii.

The ligation product was then introduced by electroporation into E. coli DH10β.

The ampicillin-resistant transformants were selected and the presence of the insert was verified by extraction of the plasmid DNA and digestion with the XhoI and KpnI enzymes.

The construct was then verified by sequencing using the following primers: N2Ag.XhoI; N2Ag.KpnI; TP.ndh.R; TP.ndh.F; rbcS2.3'.F.

After having verified that the sequence and the insert were correct, this plasmid, called pXX6N2Ag, is used to cotransform, by the glass beads technique, the CW15 strain of Chlamydomonas with the aphVIII plasmid that carries paromomycin resistance, and the 388 strain (auxotrophic for arginine) of Chlamydomonas with the pArg plasmid that carries the Arg7 gene encoding arginosuccinate lyase.

What is claimed is:

1. A method for increasing the capacity of a green alga to produce hydrogen, comprising transforming said alga with a polynucleotide encoding a type II NAD(P)H dehydrogenase (NDH-II), wherein said NDH-II: (a) has at least one copy of the consensus motif GxGxxG in its sequence, where "G" represents a glycine and "x" represents any amino acid, and (b) has the ability to catalyze the reduction of quinones of electron transport chains through the oxidation of NADH or NADP, using a flavin cofactor, and (c) acts as a monomer of 30 to 60 kDa or as a homodimer; and wherein said transformation results in expression of said NDH-II in said alga.

2. The method as claimed in claim 1, wherein said NDH-II is a mutant NDH-II, obtained from an NDH-II that preferentially uses NADH, by substitution of the glutamate or aspartate residue located at the end of the second beta-sheet of the pyridine-nucleotide-binding beta-alpha-beta motif, with a neutral polar residue.

3. The method as claimed in claim 1, wherein said NDH-II is chosen from:
   the NDH-II Agtundh2 from *Agrobacterium tumefaciens*, defined by the sequence SEQ ID NO: 2, or a mutant NDH-II obtained from Agtundh2 by substitution of the glutamate residue at position 201 of the sequence SEQ ID NO: 2, with a glutamine residue;
   the NDH-II N2Cr2 from *Chlamydomonas reinhardtii*, defined by the sequence SEQ ID NO: 4, or by a fragment thereof comprising amino acids 67-619 of the sequence SEQ ID NO: 4, or a mutant NDH-II obtained from N2Cr2 by substitution of the glutamate residue at position 285 of the sequence SEQ ID NO: 4, with a glutamine residue.

4. A green alga transformed with a polynucleotide encoding an NDH-II, wherein said NDH-II: (a) has at least one copy of the consensus motif GxGxxG in its sequence, where "G" represents a glycine and "x" represents any amino acid, and (b) has the ability to catalyze the reduction of quinones of electron transport chains through the oxidation of NADH or NADP, using a flavin cofactor, and (c) acts as a monomer of 30 to 60 kDa or as a homodimer; and wherein said transformation results in expression of said NDH-II in said alga.

5. A green alga transformed with a polynucleotide encoding an NDH-II, wherein said NDH-II: (a) has at least one copy of the consensus motif GxGxxG in its sequence, where "G" represents a glycine and "x" represents any amino acid, and (b) has the ability to catalyze the reduction of quinones of electron transport chains through the oxidation of NADH or NADP, using a flavin cofactor, and (c) acts as a monomer of 30 to 60 kDa or as a homodimer; wherein said transformation results in expression of said NDH-II in said alga; and wherein said NDH-II is a mutant NDH-II, obtained from an NDH-II that preferentially uses NADH, by substitution of the glutamate or aspartate residue located at the end of the second beta-sheet of the pyridine-nucleotide-binding beta-alpha-beta motif, with a neutral polar residue.

6. A green alga transformed with a polynucleotide encoding an NDH-II, wherein said NDH-II: (a) has at least one copy of the consensus motif GxGxxG in its sequence, where "G" represents a glycine and "x" represents any amino acid, and (b) has the ability to catalyze the reduction of quinones of electron transport chains through the oxidation of NADH or NADP, using a flavin cofactor, and (c) acts as a monomer of 30 to 60 kDa or as a homodimer; wherein said transformation results in expression of said NDH-II in said alga; and wherein said NDH-II is chosen from:
   the NDH-II Agtundh2 from *Agrobacterium tumefaciens*, defined by the sequence SEQ ID NO: 2,or a mutant NDH-II obtained from Agtundh2 by substitution of the glutamate residue at position 201 of the sequence SEQ ID NO: 2, with a glutamine residue;
   the NDH-II N2Cr2 from *Chlamydomonas reinhardtii*, defined by the sequence SEQ ID NO: 4, or by a fragment thereof comprising amino acids 67-619 of the sequence SEQ ID NO: 4, or a mutant NDH-II obtained from N2Cr2 by substitution of the glutamate residue at position 285 of the sequence SEQ ID NO: 4, with a glutamine residue.

7. The method as claimed in claim 1, wherein the NDH-II is selected from the group consisting of:

the NDH-IIs from *Acidianus ambivalens* encoded by the gene identified by NCBI accession number AJ489504, the NDH-II from *Corynebacterium glutamicum* identified by NCBI accession number CAB41413.1, the NDH-II from *Escherichia coli* identified by NCBI accession number NP-415627, the NDH-II from *Synechocystis* sp, identified by NCBI accession number BAA17783, the NDH-II from *Zymomonas mobilis* identified by NCBI accession number AAD56918, the NDH-II from *Bacillus subtilis* identified by NCBI accession number NP-389111, the NDH-II from *Azotobacter vinelandi* identified by NCBI accession number AAK19737, the NDH-II from *Trypanosoma brucei* identified by NCBI accession number AAM95239.1, the NDH-II from *Solanum tuberosum* identified by NCBI accession number CAB52796.1 or CAB52797.1, the NDH-II from *Saccharomyces cerevisiae* identified by NCBI accession number NP-013586, NP-013865.1, or NP-010198.1, the NDH-II from *Neurospora crassa* identified by NCBI accession number CAB41986 or EAA27430, and the NDH-II from *Yarrowia lipolytica* identified by NCBI accession number XP-505856.

* * * * *

SEQUENCE LISTING

<160> NUMBER OF SEQ ID NOS: 38

<210> SEQ ID NO 1
<211> LENGTH: 1266
<212> TYPE: DNA

```
<213> ORGANISM: Agrobacterium tumefaciens
<220> FEATURE:
<221> NAME/KEY: CDS
<222> LOCATION: (1)..(1266)

<400> SEQUENCE: 1 atg caa gaa cat cat gtt gtc gtc gtg ggt gga ggc ttc ggc ggt tta        48
Met Gln Glu His His Val Val Val Val Gly Gly Gly Phe Gly Gly Leu
1               5                   10                  15 caa ctg gtg cat ggg ctg gag ggg gcc cct gtc cgc att aca tta atc        96
Gln Leu Val His Gly Leu Glu Gly Ala Pro Val Arg Ile Thr Leu Ile
                20                  25                  30 gac cgt cgc aat cac cac ctg ttt cag ccc ctg ctg tat cag gtt gcg       144
Asp Arg Arg Asn His His Leu Phe Gln Pro Leu Leu Tyr Gln Val Ala
            35                  40                  45 acg acg gcg ctg gcg aca tcc gag atc gcc tgg ccg atc cgc cat ctt       192
Thr Thr Ala Leu Ala Thr Ser Glu Ile Ala Trp Pro Ile Arg His Leu
        50                  55                  60 tac cgc gac cgc aag gaa gtg acg acc ctg ctt gcg gag gtg acc ggc       240
Tyr Arg Asp Arg Lys Glu Val Thr Thr Leu Leu Ala Glu Val Thr Gly
65                  70                  75                  80 gtg gac cgg gcg gcg cgg acc gtg cag ctg aat tcg ggc cag gtg atc       288
Val Asp Arg Ala Ala Arg Thr Val Gln Leu Asn Ser Gly Gln Val Ile
                85                  90                  95 ggc ttc gat acg ctg gtg ctg gcc acc ggc gcg cgt cac gcc tat ttc       336
Gly Phe Asp Thr Leu Val Leu Ala Thr Gly Ala Arg His Ala Tyr Phe
                100                 105                 110 ggt cac gac gaa tgg gag cgt tcc gcc ccc ggc ctc aag acg ctg gaa       384
Gly His Asp Glu Trp Glu Arg Ser Ala Pro Gly Leu Lys Thr Leu Glu
            115                 120                 125 gat gca acg aca atc cgc cgc cgc ctg ctt ctg gcc ttc gaa agg gcc       432
Asp Ala Thr Thr Ile Arg Arg Arg Leu Leu Leu Ala Phe Glu Arg Ala
        130                 135                 140 gaa ctt gcc acc agt gaa gag gag cgg cag gcg ctg ctg acc ttc gtc       480
Glu Leu Ala Thr Ser Glu Glu Glu Arg Gln Ala Leu Leu Thr Phe Val
145                 150                 155                 160 atc atc ggg gcc ggc ccg acc ggc gtg gaa atg gcg ggc atg atc gcc       528
Ile Ile Gly Ala Gly Pro Thr Gly Val Glu Met Ala Gly Met Ile Ala
                165                 170                 175 gag ctc gcc cac agg gcg ctg ccg gcg gaa ttc gcc aat gtc gat acc       576
Glu Leu Ala His Arg Ala Leu Pro Ala Glu Phe Arg Asn Val Asp Thr
            180                 185                 190 aga aag acc cgc gta ttg ctt gtg gag gcc ggc cct cgc gtc ctg ccg       624
Arg Lys Thr Arg Val Leu Leu Val Glu Ala Gly Pro Arg Val Leu Pro
        195                 200                 205 gtc ttc acg gag gat ctt tcg acc tat gcg aag gaa gcg ctt gag aag       672
Val Phe Thr Glu Asp Leu Ser Thr Tyr Ala Lys Glu Ala Leu Glu Lys
    210                 215                 220 ctc ggc gtc gag gtt ctc ctc gga acg ccg gtg acg gcc tgc acg gat       720
Leu Gly Val Glu Val Leu Leu Gly Thr Pro Val Thr Ala Cys Thr Asp
225                 230                 235                 240 gag ggc gtg acg gtg ggc gag acc tat tat ccc tgc cgc acc gtc gtc       768
Glu Gly Val Thr Val Gly Glu Thr Tyr Tyr Pro Cys Arg Thr Val Val
                245                 250                 255 tgg gcc gcc ggt gtg cag gcc tct ccg gca gcg aag tgg ctg aat gcg       816
Trp Ala Ala Gly Val Gln Ala Ser Pro Ala Ala Lys Trp Leu Asn Ala
            260                 265                 270 gcc ggc gac agg gca ggg cgt gtc atc gtc ggg ccg cag ctt cat ctc       864
Ala Gly Asp Arg Ala Gly Arg Val Ile Val Gly Pro Gln Leu His Leu
        275                 280                 285 gaa gac gat gct gat atc ttc gtc atc ggc gat acc gcc gcg gtc aat       912
```

```
                          gaa aac ggc aag ccg gtg ccg ggc atc gcg ccc gcg gca aag cag      960
Glu Asp Asp Ala Asp Ile Phe Val Ile Gly Asp Thr Ala Ala Val Asn
    290                 295                 300
cag gaa aac ggc aag ccg gtg ccg ggc atc gcg ccc gcg gca aag cag      960
Gln Glu Asn Gly Lys Pro Val Pro Gly Ile Ala Pro Ala Ala Lys Gln
305                 310                 315                 320 cag ggc gct tat gtg gca aag gtc atc aag gcg cga ctg gag ggc aag     1008
Gln Gly Ala Tyr Val Ala Lys Val Ile Lys Ala Arg Leu Glu Gly Lys
                325                 330                 335 ccg ata ccg gca ccc ttc cgc tac agc cat cag ggc aat ctc gcc acc     1056
Pro Ile Pro Ala Pro Phe Arg Tyr Ser His Gln Gly Asn Leu Ala Thr
            340                 345                 350 atc ggc aaa cgc gcg gcg gtg atc gat ttc ggc cgg ttc aag ctg aag     1104
Ile Gly Lys Arg Ala Ala Val Ile Asp Phe Gly Arg Phe Lys Leu Lys
        355                 360                 365 ggc gtg ctg gca tgg tgg ata tgg ggg ctt gcc cat atc tac ttc ctg     1152
Gly Val Leu Ala Trp Trp Ile Trp Gly Leu Ala His Ile Tyr Phe Leu
    370                 375                 380 atc gga acg cgg tcg cgg ctg gcc gtg gcg tgg agc tgg ctg tgg att     1200
Ile Gly Thr Arg Ser Arg Leu Ala Val Ala Trp Ser Trp Leu Trp Ile
385                 390                 395                 400 tat ctg agc ggc cag cac agt gcg cgc ctg att acc cag aaa gag acg     1248
Tyr Leu Ser Gly Gln His Ser Ala Arg Leu Ile Thr Gln Lys Glu Thr
                405                 410                 415 ctg aag gac gag gcc tga                                             1266
Leu Lys Asp Glu Ala
            420

<210> SEQ ID NO 2
<211> LENGTH: 421
<212> TYPE: PRT
<213> ORGANISM: Agrobacterium tumefaciens

<400> SEQUENCE: 2

Met Gln Glu His His Val Val Val Gly Gly Phe Gly Gly Leu
1               5                   10                  15

Gln Leu Val His Gly Leu Glu Gly Ala Pro Val Arg Ile Thr Leu Ile
                20                  25                  30

Asp Arg Arg Asn His His Leu Phe Gln Pro Leu Leu Tyr Gln Val Ala
            35                  40                  45

Thr Thr Ala Leu Ala Thr Ser Glu Ile Ala Trp Pro Ile Arg His Leu
        50                  55                  60

Tyr Arg Asp Arg Lys Glu Val Thr Thr Leu Leu Ala Glu Val Thr Gly
65                  70                  75                  80

Val Asp Arg Ala Ala Arg Thr Val Gln Leu Asn Ser Gly Gln Val Ile
                85                  90                  95

Gly Phe Asp Thr Leu Val Leu Ala Thr Gly Ala Arg His Ala Tyr Phe
            100                 105                 110

Gly His Asp Glu Trp Glu Arg Ser Ala Pro Gly Leu Lys Thr Leu Glu
        115                 120                 125

Asp Ala Thr Thr Ile Arg Arg Leu Leu Leu Ala Phe Glu Arg Ala
    130                 135                 140

Glu Leu Ala Thr Ser Glu Glu Glu Arg Gln Ala Leu Leu Thr Phe Val
145                 150                 155                 160

Ile Ile Gly Ala Gly Pro Thr Gly Val Glu Met Ala Gly Met Ile Ala
                165                 170                 175

Glu Leu Ala His Arg Ala Leu Pro Ala Glu Phe Arg Asn Val Asp Thr
            180                 185                 190

Arg Lys Thr Arg Val Leu Leu Val Glu Ala Gly Pro Arg Val Leu Pro
```

```
                    195                 200                 205
Val Phe Thr Glu Asp Leu Ser Thr Tyr Ala Lys Glu Ala Leu Glu Lys
    210                 215                 220

Leu Gly Val Glu Val Leu Leu Gly Thr Pro Val Thr Ala Cys Thr Asp
225                 230                 235                 240

Glu Gly Val Thr Val Gly Glu Thr Tyr Tyr Pro Cys Arg Thr Val Val
                245                 250                 255

Trp Ala Ala Gly Val Gln Ala Ser Pro Ala Ala Lys Trp Leu Asn Ala
            260                 265                 270

Ala Gly Asp Arg Ala Gly Arg Val Ile Val Gly Pro Gln Leu His Leu
        275                 280                 285

Glu Asp Asp Ala Asp Ile Phe Val Ile Gly Asp Thr Ala Ala Val Asn
    290                 295                 300

Gln Glu Asn Gly Lys Pro Val Pro Gly Ile Ala Pro Ala Ala Lys Gln
305                 310                 315                 320

Gln Gly Ala Tyr Val Ala Lys Val Ile Lys Ala Arg Leu Glu Gly Lys
                325                 330                 335

Pro Ile Pro Ala Pro Phe Arg Tyr Ser His Gln Gly Asn Leu Ala Thr
            340                 345                 350

Ile Gly Lys Arg Ala Ala Val Ile Asp Phe Gly Arg Phe Lys Leu Lys
        355                 360                 365

Gly Val Leu Ala Trp Trp Ile Trp Gly Leu Ala His Ile Tyr Phe Leu
    370                 375                 380

Ile Gly Thr Arg Ser Arg Leu Ala Val Ala Trp Ser Trp Leu Trp Ile
385                 390                 395                 400

Tyr Leu Ser Gly Gln His Ser Ala Arg Leu Ile Thr Gln Lys Glu Thr
                405                 410                 415

Leu Lys Asp Glu Ala
            420

<210> SEQ ID NO 3
<211> LENGTH: 1857
<212> TYPE: DNA
<213> ORGANISM: Chlamydomonas reinhardtii
<220> FEATURE:
<221> NAME/KEY: CDS
<222> LOCATION: (1)..(1857)

<400> SEQUENCE: 3 atg aac atg ttg ctt caa caa cag aag ctc gct gcg ggc tgc aag cag     48
Met Asn Met Leu Leu Gln Gln Gln Lys Leu Ala Ala Gly Cys Lys Gln
1               5                   10                  15 cgc agc gtt gcg cag ccc tcg cgc gga tgc gtc gct gcc cac acc ggc     96
Arg Ser Val Ala Gln Pro Ser Arg Gly Cys Val Ala Ala His Thr Gly
            20                  25                  30 ctg cgc tct ggg cgc gtt gct tcc cgt caa cga tca gtg acg act gcg    144
Leu Arg Ser Gly Arg Val Ala Ser Arg Gln Arg Ser Val Thr Thr Ala
        35                  40                  45 gtc atg aca ccg ccg gcg aag tcg gag tct tcg agc ccg gta tat acc    192
Val Met Thr Pro Pro Ala Lys Ser Glu Ser Ser Ser Pro Val Tyr Thr
    50                  55                  60 acc atg agc ctt gat ggc caa aac ctc aag act gct aag cct cgc ctg    240
Thr Met Ser Leu Asp Gly Gln Asn Leu Lys Thr Ala Lys Pro Arg Leu
65                  70                  75                  80 gtt gtg ctg ggt tcc ggc tgg ggc gcc atg tcg ttc ctg aag gcg ctg    288
Val Val Leu Gly Ser Gly Trp Gly Ala Met Ser Phe Leu Lys Ala Leu
                85                  90                  95 ccg acc agc atc agc tcg acc tat gag ctc atc gtc gtc tcg cct cgc    336
```

```
                                                                    -continued Pro Thr Ser Ile Ser Ser Thr Tyr Glu Leu Ile Val Val Ser Pro Arg
            100                 105                 110 aac tac ttc ctg tac acg ccg ctg ctg ccg gct gtg gcg acc gga acc    384
Asn Tyr Phe Leu Tyr Thr Pro Leu Leu Pro Ala Val Ala Thr Gly Thr
            115                 120                 125 atg gag gag cgt tcc att gtg gag ccc gtg cgc aac ttc atc gtg ggc    432
Met Glu Glu Arg Ser Ile Val Glu Pro Val Arg Asn Phe Ile Val Gly
        130                 135                 140 aag ggc gag ttc tac gag gct ctg tgc aag gac att gac ccg gtc gcc    480
Lys Gly Glu Phe Tyr Glu Ala Leu Cys Lys Asp Ile Asp Pro Val Ala
145                 150                 155                 160 aag gag ctg gtg tgc tgc ttc ccg gag gac gcg ggg ctg gac agc gcc    528
Lys Glu Leu Val Cys Cys Phe Pro Glu Asp Ala Gly Leu Asp Ser Ala
                165                 170                 175 tgc ttc aag atg agc tac gac gtg ctg gtc atg gcg gtc ggt tca gtg    576
Cys Phe Lys Met Ser Tyr Asp Val Leu Val Met Ala Val Gly Ser Val
            180                 185                 190 aac aac acg ttt ggc atc aag gga gtg gac cag tac tgc ttc tac ttc    624
Asn Asn Thr Phe Gly Ile Lys Gly Val Asp Gln Tyr Cys Phe Tyr Phe
            195                 200                 205 aag tcc att gag gac gcc aac agg ctg cgc tcg cgc gtg tcg gag tgc    672
Lys Ser Ile Glu Asp Ala Asn Arg Leu Arg Ser Arg Val Ser Glu Cys
210                 215                 220 ttt gag cgc gcc gcc ctg cct gcc aca ccc gag gag gag cgc aag aag    720
Phe Glu Arg Ala Ala Leu Pro Ala Thr Pro Glu Glu Glu Arg Lys Lys
225                 230                 235                 240 ctg ctg acg ttt gtg gtg gtg ggc ggc ggc ccc acg ggc gtg gag gtg    768
Leu Leu Thr Phe Val Val Val Gly Gly Gly Pro Thr Gly Val Glu Val
                245                 250                 255 gcg gcg gag ctg tac gac atg atc gag gag gac ctc tcc aag ctc tac    816
Ala Ala Glu Leu Tyr Asp Met Ile Glu Glu Asp Leu Ser Lys Leu Tyr
            260                 265                 270 ccc aac ctg gtc aag gac gtg tcc atc cag gtg gtg gag ctg atg gac    864
Pro Asn Leu Val Lys Asp Val Ser Ile Gln Val Val Glu Leu Met Asp
            275                 280                 285 cac gtg ctg tcc acc tac gac cgc gcc att agc ctg tac acc gcc gag    912
His Val Leu Ser Thr Tyr Asp Arg Ala Ile Ser Leu Tyr Thr Ala Glu
        290                 295                 300 cag ttc aag cgc gcg ggc atc aag ctg gtc ctc aac agt cgt gtg gcg    960
Gln Phe Lys Arg Ala Gly Ile Lys Leu Val Leu Asn Ser Arg Val Ala
305                 310                 315                 320 tcc gtg gag gac ggc gtg gtg cgg gtg gtg aac aag gcc aac gag agc    1008
Ser Val Glu Asp Gly Val Val Arg Val Val Asn Lys Ala Asn Glu Ser
                325                 330                 335 gtc gac atc aag ttt ggc gcg tgt gtg tgg gcc act ggc atc gcc atg    1056
Val Asp Ile Lys Phe Gly Ala Cys Val Trp Ala Thr Gly Ile Ala Met
            340                 345                 350 aac ccg ctg gtg cgg cag ctg cag gag aag ctg ccg ggg cag agc cac    1104
Asn Pro Leu Val Arg Gln Leu Gln Glu Lys Leu Pro Gly Gln Ser His
            355                 360                 365 ttc agg tct gtg ctg aca gat gac tgc atg cgc gtc aag ggc agc gac    1152
Phe Arg Ser Val Leu Thr Asp Asp Cys Met Arg Val Lys Gly Ser Asp
        370                 375                 380 ggc tcc atc tgg gcg ctg ggc gac gcc gcc acc att gac cag ccc aag    1200
Gly Ser Ile Trp Ala Leu Gly Asp Ala Ala Thr Ile Asp Gln Pro Lys
385                 390                 395                 400 gcg ctg gac tat gcc gag cag ctg ttt gag cag gcc gac acc aac cgc    1248
Ala Leu Asp Tyr Ala Glu Gln Leu Phe Glu Gln Ala Asp Thr Asn Arg
                405                 410                 415 gat ggc cgc cta agc ttg gag gag ctg cgg gtg ctg ctc aac acc gca    1296
```

| | | |
|---|---|---|
| Asp Gly Arg Leu Ser Leu Glu Glu Leu Arg Val Leu Leu Asn Thr Ala<br>           420                  425                  430 | | |

```
tcc aag gag ttc agc cac ctg gag gag cac gcg cgc ttc ctg gac agc    1344
Ser Lys Glu Phe Ser His Leu Glu Glu His Ala Arg Phe Leu Asp Ser
        435                 440                 445 caa acc ggc gtc aag cgc ttc ggc ggc ctg gtc gcc aag tcg ctc agt    1392
Gln Thr Gly Val Lys Arg Phe Gly Gly Leu Val Ala Lys Ser Leu Ser
    450                 455                 460 ccg gcg gat gcg gcg gcg gcg gcc agc aac agc agc cag ccc ttt        1440
Pro Ala Asp Ala Ala Ala Ala Ala Ser Asn Ser Ser Gln Pro Phe
465                 470                 475                 480 gcg gtg ctg ctg gac ggc aat acg gag atc tcc aag gag cag ttc aag    1488
Ala Val Leu Leu Asp Gly Asn Thr Glu Ile Ser Lys Glu Gln Phe Lys
                485                 490                 495 gac att ctt ggc aag gtg gac aag ggc ctt cgc gcg ctg cct gcc acg    1536
Asp Ile Leu Gly Lys Val Asp Lys Gly Leu Arg Ala Leu Pro Ala Thr
                500                 505                 510 gcg cag gtg gcc aac cag cag ggc aag tac ctg gcg gcg gtg ttt gcg    1584
Ala Gln Val Ala Asn Gln Gln Gly Lys Tyr Leu Ala Ala Val Phe Ala
            515                 520                 525 ggc aac cgc gtc acg ggg gcc ccg gag ctg gac gca gcg ctg gcg gac    1632
Gly Asn Arg Val Thr Gly Ala Pro Glu Leu Asp Ala Ala Leu Ala Asp
530                 535                 540 aag atc aag ccc ttc agg tac ttc cac aag ggc tcg gcc gcc tac gtg    1680
Lys Ile Lys Pro Phe Arg Tyr Phe His Lys Gly Ser Ala Ala Tyr Val
545                 550                 555                 560 ggc agc gac aag gcc gtg ttc gac ctg ccc aag ttc ggg ccg ctc acg    1728
Gly Ser Asp Lys Ala Val Phe Asp Leu Pro Lys Phe Gly Pro Leu Thr
                565                 570                 575 ggc acg ggc gcg ggc ttt gtg tgg aag agc tac gag acg atg tcg cag    1776
Gly Thr Gly Ala Gly Phe Val Trp Lys Ser Tyr Glu Thr Met Ser Gln
                580                 585                 590 ttc tcc ttc cgc aac cag tgt ctg gtc gcc gcc gac tgg ctg cgc acc    1824
Phe Ser Phe Arg Asn Gln Cys Leu Val Ala Ala Asp Trp Leu Arg Thr
            595                 600                 605 aag atc ttt ggc cgc gac atc tcg cga gtg tga                        1857
Lys Ile Phe Gly Arg Asp Ile Ser Arg Val
610                 615

<210> SEQ ID NO 4
<211> LENGTH: 618
<212> TYPE: PRT
<213> ORGANISM: Chlamydomonas reinhardtii

<400> SEQUENCE: 4

Met Asn Met Leu Leu Gln Gln Gln Lys Leu Ala Ala Gly Cys Lys Gln
1               5                   10                  15

Arg Ser Val Ala Gln Pro Ser Arg Gly Cys Val Ala Ala His Thr Gly
            20                  25                  30

Leu Arg Ser Gly Arg Val Ala Ser Arg Gln Arg Ser Val Thr Thr Ala
        35                  40                  45

Val Met Thr Pro Pro Ala Lys Ser Glu Ser Ser Pro Val Tyr Thr
    50                  55                  60

Thr Met Ser Leu Asp Gly Gln Asn Leu Lys Thr Ala Lys Pro Arg Leu
65                  70                  75                  80

Val Val Leu Gly Ser Gly Trp Gly Ala Met Ser Phe Leu Lys Ala Leu
                85                  90                  95

Pro Thr Ser Ile Ser Ser Thr Tyr Glu Leu Ile Val Val Ser Pro Arg
                100                 105                 110
```

```
Asn Tyr Phe Leu Tyr Thr Pro Leu Pro Ala Val Ala Thr Gly Thr
            115                 120                 125

Met Glu Glu Arg Ser Ile Val Glu Pro Val Arg Asn Phe Ile Val Gly
    130                 135                 140

Lys Gly Glu Phe Tyr Glu Ala Leu Cys Lys Asp Ile Asp Pro Val Ala
145                 150                 155                 160

Lys Glu Leu Val Cys Cys Phe Pro Glu Asp Ala Gly Leu Asp Ser Ala
                165                 170                 175

Cys Phe Lys Met Ser Tyr Asp Val Leu Val Met Ala Val Gly Ser Val
                180                 185                 190

Asn Asn Thr Phe Gly Ile Lys Gly Val Asp Gln Tyr Cys Phe Tyr Phe
            195                 200                 205

Lys Ser Ile Glu Asp Ala Asn Arg Leu Arg Ser Arg Val Ser Glu Cys
210                 215                 220

Phe Glu Arg Ala Ala Leu Pro Ala Thr Pro Glu Glu Arg Lys Lys
225                 230                 235                 240

Leu Leu Thr Phe Val Val Gly Gly Pro Thr Gly Val Glu Val
                245                 250                 255

Ala Ala Glu Leu Tyr Asp Met Ile Glu Glu Asp Leu Ser Lys Leu Tyr
            260                 265                 270

Pro Asn Leu Val Lys Asp Val Ser Ile Gln Val Val Glu Leu Met Asp
                275                 280                 285

His Val Leu Ser Thr Tyr Asp Arg Ala Ile Ser Leu Tyr Thr Ala Glu
            290                 295                 300

Gln Phe Lys Arg Ala Gly Ile Lys Leu Val Leu Asn Ser Arg Val Ala
305                 310                 315                 320

Ser Val Glu Asp Gly Val Val Arg Val Val Asn Lys Ala Asn Glu Ser
                325                 330                 335

Val Asp Ile Lys Phe Gly Ala Cys Val Trp Ala Thr Gly Ile Ala Met
                340                 345                 350

Asn Pro Leu Val Arg Gln Leu Gln Glu Lys Leu Pro Gly Gln Ser His
            355                 360                 365

Phe Arg Ser Val Leu Thr Asp Asp Cys Met Arg Val Lys Gly Ser Asp
            370                 375                 380

Gly Ser Ile Trp Ala Leu Gly Asp Ala Ala Thr Ile Asp Gln Pro Lys
385                 390                 395                 400

Ala Leu Asp Tyr Ala Glu Gln Leu Phe Glu Gln Ala Asp Thr Asn Arg
                405                 410                 415

Asp Gly Arg Leu Ser Leu Glu Glu Leu Arg Val Leu Leu Asn Thr Ala
                420                 425                 430

Ser Lys Glu Phe Ser His Leu Glu His Ala Arg Phe Leu Asp Ser
            435                 440                 445

Gln Thr Gly Val Lys Arg Phe Gly Gly Leu Val Ala Lys Ser Leu Ser
    450                 455                 460

Pro Ala Asp Ala Ala Ala Ala Ser Asn Ser Ser Gln Pro Phe
465                 470                 475                 480

Ala Val Leu Leu Asp Gly Asn Thr Glu Ile Ser Lys Glu Gln Phe Lys
                485                 490                 495

Asp Ile Leu Gly Lys Val Asp Lys Gly Leu Arg Ala Leu Pro Ala Thr
                500                 505                 510

Ala Gln Val Ala Asn Gln Gln Gly Lys Tyr Leu Ala Ala Val Phe Ala
            515                 520                 525

Gly Asn Arg Val Thr Gly Ala Pro Glu Leu Asp Ala Ala Leu Ala Asp
530                 535                 540
```

```
Lys Ile Lys Pro Phe Arg Tyr Phe His Lys Gly Ser Ala Ala Tyr Val
545                 550                 555                 560

Gly Ser Asp Lys Ala Val Phe Asp Leu Pro Lys Phe Gly Pro Leu Thr
                565                 570                 575

Gly Thr Gly Ala Gly Phe Val Trp Lys Ser Tyr Glu Thr Met Ser Gln
            580                 585                 590

Phe Ser Phe Arg Asn Gln Cys Leu Val Ala Ala Asp Trp Leu Arg Thr
            595                 600                 605

Lys Ile Phe Gly Arg Asp Ile Ser Arg Val
        610                 615

<210> SEQ ID NO 5
<211> LENGTH: 27
<212> TYPE: DNA
<213> ORGANISM: Artificial
<220> FEATURE:
<223> OTHER INFORMATION: N2Ag.mfe.F

<400> SEQUENCE: 5
cgccaattga tgcaagaaca tcatgtt                                    27

<210> SEQ ID NO 6
<211> LENGTH: 48
<212> TYPE: DNA
<213> ORGANISM: Artificial
<220> FEATURE:
<223> OTHER INFORMATION: N2Ag.6His.PstR

<400> SEQUENCE: 6
aaaactgcag tcaatgatga tgatgatgat gggcctcgtc cttcagcg             48

<210> SEQ ID NO 7
<211> LENGTH: 18
<212> TYPE: DNA
<213> ORGANISM: Artificial
<220> FEATURE:
<223> OTHER INFORMATION: PSD80.F

<400> SEQUENCE: 7
gagctgttga caattaat                                              18

<210> SEQ ID NO 8
<211> LENGTH: 18
<212> TYPE: DNA
<213> ORGANISM: Artificial
<220> FEATURE:
<223> OTHER INFORMATION: PSD80.R

<400> SEQUENCE: 8
aggacgggtc acacgcgc                                              18

<210> SEQ ID NO 9
<211> LENGTH: 17
<212> TYPE: DNA
<213> ORGANISM: Artificial
<220> FEATURE:
<223> OTHER INFORMATION: N2Ag.307.F

<400> SEQUENCE: 9
tggccaccgg cgcgcgt                                               17

<210> SEQ ID NO 10
<211> LENGTH: 18
<212> TYPE: DNA
```

```
<213> ORGANISM: Artificial
<220> FEATURE:
<223> OTHER INFORMATION: N2Ag.650.f

<400> SEQUENCE: 10
tgcgaaggaa gcgcttga                                              18

<210> SEQ ID NO 11
<211> LENGTH: 17
<212> TYPE: DNA
<213> ORGANISM: Artificial
<220> FEATURE:
<223> OTHER INFORMATION: N2Ag.901.R

<400> SEQUENCE: 11
ttcctgattg accgcgg                                               17

<210> SEQ ID NO 12
<211> LENGTH: 27
<212> TYPE: DNA
<213> ORGANISM: Artificial
<220> FEATURE:
<223> OTHER INFORMATION: ndhAgTu.F

<400> SEQUENCE: 12
tcccccggga tgcaagaaca tcatgtt                                    27

<210> SEQ ID NO 13
<211> LENGTH: 27
<212> TYPE: DNA
<213> ORGANISM: Artificial
<220> FEATURE:
<223> OTHER INFORMATION: ndhAgTu.R

<400> SEQUENCE: 13
ccgcaattgt caggcctcgt ccttcag                                    27

<210> SEQ ID NO 14
<211> LENGTH: 24
<212> TYPE: DNA
<213> ORGANISM: Artificial
<220> FEATURE:
<223> OTHER INFORMATION: N2Ag.NcoI

<400> SEQUENCE: 14
atggaagaac atcatgttgt cgtc                                       24

<210> SEQ ID NO 15
<211> LENGTH: 30
<212> TYPE: DNA
<213> ORGANISM: Artificial
<220> FEATURE:
<223> OTHER INFORMATION: N2Ag.XbaI

<400> SEQUENCE: 15
ccgtctagat caggcctcgt ccttcagcgt                                 30

<210> SEQ ID NO 16
<211> LENGTH: 21
<212> TYPE: DNA
<213> ORGANISM: Artificial
<220> FEATURE:
<223> OTHER INFORMATION: N2Ag.E203Q.R

<400> SEQUENCE: 16
agggccggcc tgcacaagca a                                          21
```

<210> SEQ ID NO 17
<211> LENGTH: 21
<212> TYPE: DNA
<213> ORGANISM: Artificial
<220> FEATURE:
<223> OTHER INFORMATION: N2Ag.E203Q.F

<400> SEQUENCE: 17
ttgcttgtgc aggccggccc t                                    21

<210> SEQ ID NO 18
<211> LENGTH: 24
<212> TYPE: DNA
<213> ORGANISM: Artificial
<220> FEATURE:
<223> OTHER INFORMATION: N2Cr2.F

<400> SEQUENCE: 18
atgcatagcc ttgatggcca aaac                                 24

<210> SEQ ID NO 19
<211> LENGTH: 21
<212> TYPE: DNA
<213> ORGANISM: Artificial
<220> FEATURE:
<223> OTHER INFORMATION: N2Cr2.R

<400> SEQUENCE: 19
tcacactcgc gagatgtcgc g                                    21

<210> SEQ ID NO 20
<211> LENGTH: 50
<212> TYPE: DNA
<213> ORGANISM: Artificial
<220> FEATURE:
<223> OTHER INFORMATION: F-EcoRI

<400> SEQUENCE: 20
cggaattcat gcatcatcat catcatcatc atagccttga tggccaaaac     50

<210> SEQ ID NO 21
<211> LENGTH: 30
<212> TYPE: DNA
<213> ORGANISM: Artificial
<220> FEATURE:
<223> OTHER INFORMATION: R-SmaI

<400> SEQUENCE: 21
tcccccgggt cacactcgcg agatgtcgcg                           30

<210> SEQ ID NO 22
<211> LENGTH: 30
<212> TYPE: DNA
<213> ORGANISM: Artificial
<220> FEATURE:
<223> OTHER INFORMATION: N2Ag.XhoI

<400> SEQUENCE: 22
cggctcgaga tggccgccgt cattgccaag                           30

<210> SEQ ID NO 23
<211> LENGTH: 48
<212> TYPE: DNA
<213> ORGANISM: Artificial
<220> FEATURE:
<223> OTHER INFORMATION: TP.ndh.R -continued

<400> SEQUENCE: 23
gacgacaaca tgatgttctt gcatctggtt ggcctgagcc ggggcagc    48

<210> SEQ ID NO 24
<211> LENGTH: 48
<212> TYPE: DNA
<213> ORGANISM: Artificial
<220> FEATURE:
<223> OTHER INFORMATION: TP.ndh.F

<400> SEQUENCE: 24
gctgccccgg ctcaggccaa ccagatgcaa gaacatcatg ttgtcgtc    48

<210> SEQ ID NO 25
<211> LENGTH: 48
<212> TYPE: DNA
<213> ORGANISM: Artificial
<220> FEATURE:
<223> OTHER INFORMATION: rbcS2.3'.R

<400> SEQUENCE: 25
gctcagatca acgagcgcct ccattcaggc ctcgtccttc agcgtctc    48

<210> SEQ ID NO 26
<211> LENGTH: 48
<212> TYPE: DNA
<213> ORGANISM: Artificial
<220> FEATURE:
<223> OTHER INFORMATION: rbcS2.3'.F

<400> SEQUENCE: 26
gagacgctga aggacgaggc ctgaatggag gcgctcgttg atctgagc    48

<210> SEQ ID NO 27
<211> LENGTH: 27
<212> TYPE: DNA
<213> ORGANISM: Artificial
<220> FEATURE:
<223> OTHER INFORMATION: N2Ag.KpnI

<400> SEQUENCE: 27
cggggtaccc tgcaaatgct gtctcca    27

<210> SEQ ID NO 28
<211> LENGTH: 54
<212> TYPE: PRT
<213> ORGANISM: Neurospora crassa

<400> SEQUENCE: 28

Ala Asn Leu Leu His Phe Ala Ile Val Gly Gly Gly Pro Thr Gly Ile
1               5                   10                  15

Glu Tyr Ala Ser Glu Leu His Asp Leu Ile His Asp Asp Leu Ser Lys
            20                  25                  30

Met Tyr Pro Asp Leu Leu Lys Phe Val Arg Ile Thr Val Tyr Asp Val
        35                  40                  45

Ser Pro Lys Val Leu Pro
    50

<210> SEQ ID NO 29
<211> LENGTH: 54
<212> TYPE: PRT
<213> ORGANISM: Chlamydomonas reinhardtii

<400> SEQUENCE: 29

```
Lys Lys Leu Leu Thr Phe Val Val Gly Gly Gly Pro Thr Gly Val
1               5                   10                  15

Glu Val Ala Ala Glu Leu Tyr Asp Met Ile Glu Asp Leu Ser Lys
            20                  25                  30

Leu Tyr Pro Asn Leu Val Lys Asp Val Ser Ile Gln Val Glu Leu
            35                  40                  45

Met Asp His Val Leu Ser
    50
```

<210> SEQ ID NO 30
<211> LENGTH: 54
<212> TYPE: PRT
<213> ORGANISM: Solanum tuberosum

<400> SEQUENCE: 30

```
Arg Thr Asn Leu His Phe Val Ile Val Gly Gly Pro Thr Gly Val
1               5                   10                  15

Glu Phe Ala Ala Glu Leu His Asp Tyr Val Tyr Glu Asp Leu Val Lys
            20                  25                  30

Ile Tyr Pro Ser Val Lys Asp Phe Val Lys Ile Thr Val Ile Gln Ser
            35                  40                  45

Gly Asp His Ile Leu Asn
    50
```

<210> SEQ ID NO 31
<211> LENGTH: 54
<212> TYPE: PRT
<213> ORGANISM: Saccharomyces cerevisiae

<400> SEQUENCE: 31

```
Ala Arg Leu Leu Ser Phe Val Val Val Gly Gly Gly Pro Thr Gly Val
1               5                   10                  15

Glu Phe Ala Ala Glu Leu Arg Asp Tyr Val Asp Gln Asp Leu Arg Lys
            20                  25                  30

Trp Met Pro Glu Leu Ser Lys Glu Ile Lys Val Thr Leu Val Glu Ala
            35                  40                  45

Leu Pro Asn Ile Leu Asn
    50
```

<210> SEQ ID NO 32
<211> LENGTH: 54
<212> TYPE: PRT
<213> ORGANISM: Saccharomyces cerevisiae

<400> SEQUENCE: 32

```
Lys Arg Leu Leu Thr Phe Val Val Gly Gly Gly Pro Thr Gly Val
1               5                   10                  15

Glu Phe Ala Ala Glu Leu Gln Asp Tyr Ile Asn Gln Asp Leu Arg Lys
            20                  25                  30

Trp Met Pro Asp Leu Ser Lys Glu Met Lys Val Ile Leu Ile Glu Ala
            35                  40                  45

Leu Pro Asn Ile Leu Asn
    50
```

<210> SEQ ID NO 33
<211> LENGTH: 54
<212> TYPE: PRT
<213> ORGANISM: Yarrowia lipolytica

<400> SEQUENCE: 33

Lys Arg Leu Leu His Thr Val Val Gly Gly Gly Pro Thr Gly Val
1               5                   10                  15

Glu Phe Ala Ala Glu Leu Gln Asp Phe Glu Asp Leu Arg Lys
            20                  25                  30

Trp Ile Pro Asp Ile Arg Asp Asp Phe Lys Val Thr Leu Val Glu Ala
            35                  40                  45

Leu Pro Asn Val Leu Pro
    50

<210> SEQ ID NO 34
<211> LENGTH: 54
<212> TYPE: PRT
<213> ORGANISM: Saccharomyces cerevisiae

<400> SEQUENCE: 34

Arg Arg Leu Leu Ser Ile Val Val Gly Gly Gly Pro Thr Gly Val
1               5                   10                  15

Glu Ala Ala Gly Glu Leu Gln Asp Tyr Val His Gln Asp Leu Arg Lys
            20                  25                  30

Phe Leu Pro Ala Leu Ala Glu Glu Val Gln Ile His Leu Val Glu Ala
            35                  40                  45

Leu Pro Ile Val Leu Asn
    50

<210> SEQ ID NO 35
<211> LENGTH: 55
<212> TYPE: PRT
<213> ORGANISM: Neurospora crassa

<400> SEQUENCE: 35

Lys Arg Leu Leu Ser Phe Val Val Cys Gly Gly Gly Pro Thr Gly Val
1               5                   10                  15

Glu Phe Ala Ala Glu Leu Phe Asp Leu Leu Asn Glu Asp Leu Thr Leu
            20                  25                  30

His Phe Pro Arg Leu Leu Arg Asn Glu Ile Ser Val His Leu Ile Gln
            35                  40                  45

Ser Arg Asp His Ile Leu Asn
    50              55

<210> SEQ ID NO 36
<211> LENGTH: 55
<212> TYPE: PRT
<213> ORGANISM: Agrobacterium tumefaciens

<400> SEQUENCE: 36

Gln Ala Leu Leu Thr Phe Val Ile Ile Gly Ala Gly Pro Thr Gly Val
1               5                   10                  15

Glu Met Ala Gly Met Ile Ala Glu Leu Ala His Arg Ala Leu Pro Ala
            20                  25                  30

Glu Phe Arg Asn Val Asp Thr Arg Lys Thr Arg Val Leu Leu Val Glu
            35                  40                  45

Ala Gly Pro Arg Val Leu Pro
    50              55

<210> SEQ ID NO 37
<211> LENGTH: 55
<212> TYPE: PRT
<213> ORGANISM: Escherichia coli str. K-12 substr. MG1655

<400> SEQUENCE: 37

-continued

```
Asn Gly Lys Val Asn Ile Ala Ile Val Gly Gly Ala Thr Gly Val
1               5                   10                  15

Glu Leu Ser Ala Glu Leu His Asn Ala Val Lys Gln Leu His Ser Tyr
            20                  25                  30

Gly Tyr Lys Gly Leu Thr Asn Glu Ala Leu Asn Val Thr Leu Val Glu
        35                  40                  45

Ala Gly Glu Arg Ile Leu Pro
    50                  55

<210> SEQ ID NO 38
<211> LENGTH: 43
<212> TYPE: PRT
<213> ORGANISM: Synechocystis sp. PCC 683

<400> SEQUENCE: 38

Ala Glu Lys Ile Arg Ile Ala Ile Val Gly Gly Gly Tyr Ser Gly Val
1               5                   10                  15

Glu Leu Ala Ala Lys Leu Gly Asp Arg Leu Gly Glu Arg Gly Arg Ile
            20                  25                  30

Arg Ile Ile Glu Gly Lys Glu Ile Leu Ala Met
        35                  40
```